(12) United States Patent
Rogers

(10) Patent No.: US 10,064,582 B2
(45) Date of Patent: Sep. 4, 2018

(54) NONINVASIVE DETERMINATION OF CARDIAC HEALTH AND OTHER FUNCTIONAL STATES AND TRENDS FOR HUMAN PHYSIOLOGICAL SYSTEMS

(71) Applicant: Google, Inc., Mountain View, CA (US)

(72) Inventor: Jeffrey L. Rogers, San Carlos, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 14/599,954

(22) Filed: Jan. 19, 2015

(65) Prior Publication Data

US 2016/0206244 A1  Jul. 21, 2016

(51) Int. Cl.
*A61B 5/00* (2006.01)
*A61B 5/021* (2006.01)
(Continued)

(52) U.S. Cl.
CPC .......... *A61B 5/6891* (2013.01); *A61B 5/0022* (2013.01); *A61B 5/021* (2013.01);
(Continued)

(58) Field of Classification Search
CPC ....... A61B 5/6891; A61B 5/746; A61B 5/021; A61B 5/1032; A61B 5/6892;
(Continued)

(56) References Cited

U.S. PATENT DOCUMENTS 5,410,471 A * 4/1995 Alyfuku ................. A61B 5/117
4/314

5,798,798 A   8/1998 Rector et al.
(Continued)

FOREIGN PATENT DOCUMENTS

| CN | 102660988 | 3/2014 |
|---|---|---|
| EP | 2417908 | 2/2012 |

(Continued)

OTHER PUBLICATIONS

Richard E. Klabunde, Ventricular Pressure-Volume Loop Changes in Valve Disease, Dec. 1, 2010, Cardiovascular Physiology Concepts, https://web.archive.org/web/20101201185256/http://cvphysiology.com/Heart%20Disease/HD009.htm.*

(Continued)

*Primary Examiner* — Aaron Roane
(74) *Attorney, Agent, or Firm* — Colby Nipper

(57) ABSTRACT

This document describes assessment of human physiological systems. Various noninvasive sensors can be used to detect vitals and other parameters and combined with mathematical models to assess the functional state of physiological systems. Conventional techniques can use invasive sensors to monitor cardiac pressures and volumes, along with pressure transit to quantify cardiovascular health. While known to be effective these invasive techniques often require surgery and are resource intensive limiting their use to cases where the risks and costs are of clear immediate benefit. In contrast, noninvasive health monitors present little if any risk and are easy to use. Further, the techniques described herein can determine trends in a person's cardiovascular health. With these trends, a person can know if the effort they expend to improve heart health actually makes a difference. Further, negative trends can be found that can spur people to improve their health or get medical attention.

18 Claims, 18 Drawing Sheets

(51) Int. Cl.

| | |
|---|---|
| *A61B 5/0205* | (2006.01) |
| *A61B 5/103* | (2006.01) |
| *A61B 5/02* | (2006.01) |
| A61B 5/05 | (2006.01) |
| A61B 5/11 | (2006.01) |
| A61B 5/01 | (2006.01) |
| A61B 5/0255 | (2006.01) |
| A61B 5/0402 | (2006.01) |
| G01K 11/00 | (2006.01) |
| A61B 8/06 | (2006.01) |
| A61B 8/08 | (2006.01) |
| A61B 8/14 | (2006.01) |
| A61B 8/00 | (2006.01) |
| A47K 13/30 | (2006.01) |

(52) U.S. Cl.
CPC ........ *A61B 5/0205* (2013.01); *A61B 5/02028* (2013.01); *A61B 5/1032* (2013.01); *A61B 5/40* (2013.01); *A61B 5/42* (2013.01); *A61B 5/441* (2013.01); *A61B 5/45* (2013.01); *A61B 5/4842* (2013.01); *A61B 5/6892* (2013.01); *A61B 5/6898* (2013.01); *A61B 5/7246* (2013.01); *A61B 5/7275* (2013.01); *A61B 5/742* (2013.01); *A61B 5/746* (2013.01); *A61B 5/747* (2013.01); *A61B 5/7475* (2013.01); *A47K 13/30* (2013.01); *A61B 5/01* (2013.01); *A61B 5/0255* (2013.01); *A61B 5/0402* (2013.01); *A61B 5/05* (2013.01); *A61B 5/1102* (2013.01); *A61B 5/1126* (2013.01); *A61B 5/4509* (2013.01); *A61B 5/4528* (2013.01); *A61B 8/06* (2013.01); *A61B 8/0875* (2013.01); *A61B 8/0883* (2013.01); *A61B 8/14* (2013.01); *A61B 8/4477* (2013.01); *A61B 8/483* (2013.01); *A61B 2505/07* (2013.01); *A61B 2562/0204* (2013.01); *A61B 2562/0233* (2013.01); *A61B 2562/0247* (2013.01); *G01K 11/006* (2013.01)

(58) Field of Classification Search
CPC ... A61B 5/0022; A61B 5/6898; A61B 5/7275; A61B 5/0205; A61B 5/747; A61B 5/02
USPC .......................................................... 600/301
See application file for complete search history.

(56) References Cited

U.S. PATENT DOCUMENTS

| | | | |
|---|---|---|---|
| 6,254,544 B1 | 7/2001 | Hayashi | |
| 6,386,757 B1 | 5/2002 | Konno | |
| 6,513,970 B1 | 2/2003 | Tabata et al. | |
| 6,524,239 B1* | 2/2003 | Reed | A61B 5/0002 128/920 |
| 6,616,613 B1 | 9/2003 | Goodman | |
| 7,194,371 B1 | 3/2007 | McBride et al. | |
| 7,421,061 B2 | 9/2008 | Boese et al. | |
| 7,647,093 B2 | 1/2010 | Bojovic et al. | |
| 7,677,729 B2 | 3/2010 | Vilser et al. | |
| 7,691,067 B2 | 4/2010 | Westbrook et al. | |
| 7,698,154 B2 | 4/2010 | Marchosky | |
| 8,062,220 B2 | 11/2011 | Kurtz et al. | |
| 8,193,929 B1 | 6/2012 | Siu et al. | |
| 8,289,185 B2 | 10/2012 | Alonso | |
| 8,301,232 B2 | 10/2012 | Albert et al. | |
| 8,475,367 B1 | 7/2013 | Yuen et al. | |
| 8,509,882 B2 | 8/2013 | Albert et al. | |
| 8,562,526 B2* | 10/2013 | Heneghan | A61B 5/0507 128/920 |
| 8,655,004 B2 | 2/2014 | Prest et al. | |
| 8,700,137 B2 | 4/2014 | Albert | |
| 8,758,020 B2 | 6/2014 | Burdea et al. | |
| 8,764,651 B2 | 7/2014 | Tran | |
| 8,790,257 B2 | 7/2014 | Libbus et al. | |
| 9,508,141 B2 | 11/2016 | Khachaturian et al. | |
| 9,848,780 B1 | 12/2017 | Debusschere et al. | |
| 2003/0093000 A1 | 5/2003 | Nishio et al. | |
| 2003/0122677 A1 | 7/2003 | Kail | |
| 2004/0102693 A1 | 5/2004 | Jenkins | |
| 2004/0249250 A1 | 12/2004 | McGee et al. | |
| 2007/0118043 A1 | 5/2007 | Oliver et al. | |
| 2007/0161921 A1 | 7/2007 | Rausch | |
| 2007/0197878 A1 | 8/2007 | Shklarski | |
| 2008/0001735 A1* | 1/2008 | Tran | G06F 19/3418 340/539.22 |
| 2008/0015422 A1 | 1/2008 | Wessel | |
| 2008/0039731 A1 | 2/2008 | McCombie et al. | |
| 2008/0194975 A1 | 8/2008 | MacQuarrie et al. | |
| 2009/0018408 A1 | 1/2009 | Ouchi et al. | |
| 2009/0253585 A1 | 10/2009 | Diatchenko et al. | |
| 2009/0270690 A1 | 10/2009 | Roos et al. | |
| 2010/0069730 A1 | 3/2010 | Bergstrom et al. | |
| 2010/0094141 A1 | 4/2010 | Puswella | |
| 2010/0179820 A1 | 7/2010 | Harrison et al. | |
| 2010/0204550 A1* | 8/2010 | Heneghan | A61B 5/0205 600/301 |
| 2010/0292549 A1 | 11/2010 | Schuler | |
| 2010/0324384 A1 | 12/2010 | Moon et al. | |
| 2011/0029038 A1 | 2/2011 | Hyde et al. | |
| 2011/0118564 A1 | 5/2011 | Sankai | |
| 2011/0202404 A1 | 8/2011 | van der Riet | |
| 2011/0213218 A1 | 9/2011 | Weiner et al. | |
| 2011/0245688 A1 | 10/2011 | Arora et al. | |
| 2012/0029369 A1 | 2/2012 | Icove et al. | |
| 2012/0123232 A1 | 5/2012 | Najarian et al. | |
| 2012/0220835 A1 | 8/2012 | Chung | |
| 2012/0310665 A1 | 12/2012 | Xu et al. | |
| 2013/0035563 A1 | 2/2013 | Angellides | |
| 2013/0053653 A1 | 2/2013 | Cuddihy et al. | |
| 2013/0096439 A1 | 4/2013 | Lee et al. | |
| 2013/0132931 A1 | 5/2013 | Bruns et al. | |
| 2013/0150735 A1 | 6/2013 | Cheng | |
| 2013/0322729 A1 | 12/2013 | Mestha et al. | |
| 2013/0345569 A1 | 12/2013 | Mestha et al. | |
| 2014/0051941 A1 | 2/2014 | Messerschmidt | |
| 2014/0072190 A1 | 3/2014 | Wu et al. | |
| 2014/0073486 A1 | 3/2014 | Ahmed et al. | |
| 2014/0073969 A1 | 3/2014 | Zou et al. | |
| 2014/0081100 A1 | 3/2014 | Muhsin et al. | |
| 2014/0121540 A1* | 5/2014 | Raskin | A61B 5/6898 600/479 |
| 2014/0139616 A1 | 5/2014 | Pinter et al. | |
| 2014/0191939 A1 | 7/2014 | Penn et al. | |
| 2014/0200416 A1 | 7/2014 | Kashef et al. | |
| 2014/0244277 A1 | 8/2014 | Krishna Rao et al. | |
| 2014/0253709 A1 | 9/2014 | Bresch et al. | |
| 2014/0275854 A1 | 9/2014 | Venkatraman et al. | |
| 2014/0297006 A1 | 10/2014 | Sadhu | |
| 2014/0376788 A1 | 12/2014 | Xu et al. | |
| 2015/0026815 A1 | 1/2015 | Barrett | |
| 2015/0046183 A1 | 2/2015 | Cireddu | |
| 2015/0099941 A1 | 4/2015 | Tran | |
| 2015/0100328 A1 | 4/2015 | Kress et al. | |
| 2015/0112606 A1 | 4/2015 | He et al. | |
| 2015/0287187 A1 | 10/2015 | Redtel | |
| 2015/0351703 A1* | 12/2015 | Phillips | A61B 8/4236 600/301 |
| 2016/0106328 A1 | 4/2016 | Mestha et al. | |
| 2016/0213331 A1 | 7/2016 | Gil et al. | |
| 2016/0220152 A1 | 8/2016 | Meriheina et al. | |
| 2016/0287172 A1 | 10/2016 | Morris et al. | |
| 2016/0321428 A1 | 11/2016 | Rogers | |
| 2016/0338599 A1 | 11/2016 | DeBusschere et al. | |
| 2018/0000354 A1 | 1/2018 | Debusschere et al. | |
| 2018/0000355 A1 | 1/2018 | Debusschere et al. | |

FOREIGN PATENT DOCUMENTS

| | | |
|---|---|---|
| JP | 113860 | 4/1999 |
| WO | WO-9001895 | 3/1990 |
| WO | WO-0127855 | 4/2001 |

(56) References Cited

FOREIGN PATENT DOCUMENTS

| WO | WO-02082999 | 10/2002 |
|---|---|---|
| WO | 2004004557 | 1/2004 |
| WO | WO-2009032073 | 3/2009 |
| WO | WO-2013186696 | 12/2013 |
| WO | WO-2013191657 | 12/2013 |
| WO | WO-2013192166 | 12/2013 |
| WO | WO-2014116968 | 7/2014 |
| WO | WO-2014124520 | 8/2014 |
| WO | WO-2014136027 | 9/2014 |
| WO | WO-2014138280 | 9/2014 |
| WO | WO-2014160893 | 10/2014 |
| WO | 2016118534 | 7/2016 |
| WO | 2016176471 | 11/2016 |
| WO | 2016178797 | 11/2016 |
| WO | 2017019299 | 2/2017 |

OTHER PUBLICATIONS

He, "A Continuous, Wearable, and Wireless Heart Monitor Using Head Ballistocardiogram (BCG) and Head Electrocardiogram (ECG) with a Nanowatt ECG Heartbeat Detection Circuit", In Proceedings: Thesis, Department of Electrical Engineering and Computer Science, Massachusetts Institute of Technology Available at: <http://dspace.mit.edu/handle/1721.1/79221>, Feb. 2013, 137 pages.

Nakajima, et al., "Development of Real-Time Image Sequence Analysis for Evaluating Posture Change and Respiratory Rate of a Subject in Bed", In Proceedings: Physiological Measurement, vol. 22, No. 3 Retrieved From: <http://iopscience.iop.org/0967-3334/22/3/401/pdf/0967-3334_22_3_401.pdf> Feb. 27, 2015, Aug. 2001, 8 pages.

"Philips Vital Signs Camera", Retrieved From: <http://www.vitalsignscamera.com/> Apr. 15, 2015, Jul. 17, 2013, 2 pages.

"Cardiio", Retrieved From: <http://www.cardiio.com/> Apr. 15, 2015 App Information Retrieved From: <https://itunes.apple.com/us/app/cardiio-touchless-camera-pulse/id542891434?ls=1&mt=8> Apr. 15, 2015, Feb. 24, 2015, 6 pages.

Balakrishnan,"Detecting Pulse from Head Motions in Video", In Proceedings: CVPR '13 Proceedings of the 2013 IEEE Conference on Computer Vision and Pattern Recognition <http://people.csail.mit.edu/mrub/vidmag/papers/Balakrishnan_Detecting_Pulse_from_2013_CVPR_paper.pdf>, Jun. 23, 2013, 8 pages.

Couderc,"Detection of Atrial Fibrillation using Contactless Facial Video Monitoring", In Proceedings: Heart Rhythm Society, vol. 12, Issue 1 Available at: <http://www.heartrhythmjournal.com/article/S1547-5271(14)00924-2/pdf>, Jan. 2015, 7 pages.

Poh,"A Medical Mirror for Non-contact Health Monitoring", In Proceedings: ACM SIGGRAPH Emerging Technologies Available at: <http://affect.media.mit.edu/pdfs/11.Poh-etal-SIGGRAPH.pdf>, 2011, 1 page.

Poh,"Non-contact, Automated Cardiac Pulse Measurements Using Video Imaging and Blind Source Separation.", In Proceedings: Optics Express, vol. 18, No. 10 Available at: <http://www.opticsinfobase.org/view_article.cfm?gotourl=http%3A%2F%2Fwww%2Eopticsinfobase%2Eorg%2FDirectPDFAccess%2F77B04D55%2DBC95%2D6937%2D5BAC49A426378C02%5F199381%2Foe%2D18%2D10%2D10762%2Ep, May 7, 2010, 13 pages.

Wang,"Exploiting Spatial Redundancy of Image Sensor for Motion Robust rPPG", In Proceedings: IEEE Transactions on Biomedical Engineering, vol. 62, Issue 2, Jan. 19, 2015, 11 pages.

"Final Office Action", U.S. Appl. No. 14/681,625, Dec. 7, 2016, 10 pages.

"International Search Report and Written Opinion", Application No. PCT/US2016/042013, Oct. 26, 2016, 12 pages.

"International Search Report and Written Opinion", Application No. PCT/US2016/033342, Oct. 27, 2016, 20 pages.

Matthews,"Venous Pulse", Retrieved at: http://www.rjmatthewsmd.com/Definitions/venous_pulse.htm—on Nov. 30, 2016, Apr. 13, 2013, 7 pages.

"International Search Report and Written Opinion", Application No. PCT/US2016/032307, Aug. 25, 2016, 13 pages.

"International Search Report and Written Opinion", Application No. PCT/US2016/029820, Jul. 15, 2016, 14 pages.

"Non-Final Office Action", U.S. Appl. No. 14/666,155, Aug. 24, 2016, 9 pages.

"Non-Final Office Action", U.S. Appl. No. 14/681,625, Aug. 12, 2016, 9 pages.

"Restriction Requirement", U.S. Appl. No. 14/666,155, Jul. 22, 2016, 5 pages.

"The Instant Blood Pressure app estimates blood pressure with your smartphone and our algorithm", Retrieved at: http://www.instantbloodpressure.com/—on Jun. 23, 2016, 6 pages.

Espina,"Wireless Body Sensor Network for Continuous Cuff-less Blood Pressure Monitoring", International Summer School on Medical Devices and Biosensors, 2006, Sep. 2006, 5 pages.

"Life:X Lifestyle eXplorer", Retrieved from <https://web.archive.org/web/20150318093841/http://research.microsoft.com/en-us/projects/lifex >, Feb. 3, 2017, 2 pages.

"Non-Final Office Action", U.S. Appl. No. 14/666,155, Feb. 3, 2017, 12 pages.

"Non-Final Office Action", U.S. Appl. No. 14/681,625, Mar. 6, 2017, 7 pages.

"Pre-Interview Communication", U.S. Appl. No. 14/715,454, Apr. 14, 2017, 3 pages.

"Pre-Interview Communication", U.S. Appl. No. 14/715,793, Mar. 20, 2017, 3 pages.

"The Dash smart earbuds play back music, and monitor your workout", Retrieved from <http://newatlas.com/bragi-dash-tracking-earbuds/30808/>, Feb. 13, 2014, 3 pages.

Palese,"The Effects of Earphones and Music on the Temperature Measured by Infrared Tympanic Thermometer: Preliminary Results", ORL—head and neck nursing: official journal of the Society of Otorhinolaryngology and Head-Neck Nurses 32.2, 2013, pp. 8-12.

"Final Office Action", U.S. Appl. No. 14/720,632, dated Jan. 9, 2018, 18 pages.

"International Preliminary Report on Patentability", PCT Application No. PCT/US2016/026756, dated Oct. 19, 2017, 8 pages.

"Non-Final Office Action", U.S. Appl. No. 14/715,454, dated Jan. 11, 2018, 16 pages.

"Non-Final Office Action", U.S. Appl. No. 14/699,181, dated Oct. 18, 2017, 33 pages.

"Notice of Allowance", U.S. Appl. No. 14/681,625, dated Oct. 23, 2017, 8 pages.

"Notice of Allowance", U.S. Appl. No. 14/715,793, dated Dec. 18, 2017, 5 pages.

"Notice of Publication", U.S. Appl. No. 15/704,615, dated Jan. 4, 2018, 1 page.

"Notice of Publication", U.S. Appl. No. 15/704,825, dated Jan. 4, 2018, 1 page.

"Pre-Interview Office Action", U.S. Appl. No. 14/731,195, dated Dec. 20, 2017, 4 pages.

"Preliminary Report on Patentability", PCT Application No. PCT/US2016/032307, dated Dec. 7, 2017, 9 pages.

"Clever Toilet Checks on Your Health", CNN.Com; Technology, dated Jun. 28, 2005, 2 pages.

"First Action Interview OA", U.S. Appl. No. 14/715,793, dated Jun. 21, 2017, 3 pages.

"First Action Interview Pilot Program Pre-Interview Communication", U.S. Appl. No. 14/731,195, dated Aug. 1, 2017, 3 pages.

"Non-Final Office Action", U.S. Appl. No. 14/720,632, dated Jun. 14, 2017, 16 pages.

"Notice of Allowance", U.S. Appl. No. 14/666,155, dated Jul. 10, 2017, 7 pages.

"Notice of Allowance", U.S. Appl. No. 14/681,625, dated Jun. 7, 2017 00:00:00.0, 7 pages.

Otto, et al., "System Architecture of a Wireless Body Area Sensor Network for Ubiquitous Health Monitoring", Journal of Mobile Multimedia; vol. 1, No. 4, Jan. 10, 2006, 20 pages.

"Apple Watch Used Four Sensors to Detect your Pulse", retrieved from http://www.theverge.com/2014/9/9/6126991/apple-watch-four-back-sensors-detect-activity on Sep. 23, 2017 as cited in PCT

(56) References Cited

OTHER PUBLICATIONS search report for PCT Application No. PCT/US2016/026756 dated Nov. 10, 2017; The Verge, paragraph 1, Sep. 9, 2014, 4 pages.
"Final Office Action", U.S. Appl. No. 14/715,454, dated Sep. 7, 2017, 14 pages.
"Final Office Action", U.S. Appl. No. 14/715,793, dated Sep. 12, 2017, 7 pages.
"Non-Invasive Quantification of Peripheral Arterial Volume Distensibilitiy and its Non-Lineaer Relationship with Arterial Pressure", Journal of Biomechanics, Pergamon Press, vol. 42, No. 8; as cited in the search report for PCT/US2016/013968 citing the whole document, but in particular the abstract, dated May 29, 2009, 2 pages.
"Pressure-Volume Loop Analysis in Cardiology", retrieved from https://en.wikipedia.org/w/index.php?t itle=Pressure-volume loop analysis in card iology&oldid=636928657 on Sep. 23, 2017; Obtained per link provided in search report from PCT/US2016/01398 dated Jul. 28, 2016, Dec. 6, 2014, 10 pages.
"Written Opinion", PCT Application No. PCT/US2016/042013, dated Feb. 2, 2017, 6 pages.
"Written Opinion", PCT Application PCT/US2016/013968, dated Jul. 28, 2016, 9 pages.
"Written Opinion", PCT Application No. PCT/US2016/026756, dated Nov. 10, 2016, 7 pages.
Ishijima, "Unobtrusive Approaches to Monitoring Vital Signs at Home", Medical & Biological Engineering and Computing, Springer, Berlin, DE, vol. 45, No. 11 as cited in search report for PCT/US2016/013968 dated Jul. 28, 2016, Sep. 26, 2007, 3 pages.
"Final Office Action", U.S. Appl. No. 14/715,454, dated Apr. 17, 2018, 19 pages.
"Notice of Allowance", U.S. Appl. No. 14/666,155, dated Feb. 20, 2018, 5 pages.
"Preliminary Report on Patentability", PCT Application No. PCT/US2016/042013, dated Jan. 30, 2018, 7 pages.
"Thermofocus No Touch Forehead Thermometer", Technimed, Internet Archive. Dec. 24, 2014. https://web.archive.org/web/20141224070848/http://www.tecnimed.it:80/thermofocus-forehead-thermometer-H1N1-swine-flu.html, Dec. 24, 2018, 4 pages.
"Final Office Action", U.S. Appl. No. 14/699,181, dated May 4, 2018, 41 pages.
"Non-Final Office Action", U.S. Appl. No. 14/720,632, dated May 18, 2018, 20 pages.
"Non-Final Office Action", U.S. Appl. No. 14/809,901, dated May 24, 2018, 13 pages.

* cited by examiner

NONINVASIVE DETERMINATION OF CARDIAC HEALTH AND OTHER FUNCTIONAL STATES AND TRENDS FOR HUMAN PHYSIOLOGICAL SYSTEMS

BACKGROUND

Cardiovascular disease is the leading cause of morbidity, mortality, and costs worldwide. At the same time this chronic disease is largely preventable. Medical science knows how to save most of these lives by removing the major risk factors of smoking, diabetes, and hypertension. And many people are told just what they need to do to reduce these risk factors—stop smoking, reduce sugar intake, eat healthier, reduce alcohol intake, increase cardiovascular exercise, lose weight, and, if needed, take blood-pressure medication. But many people do not follow this good advice. Because of this, millions of people needlessly die from cardiovascular disease.

One reason that people don't follow this good medical advice is because they think they are different, they do not want to change their behaviors that are causing the disease, or they do not know what to change in their particular case. When a physician tells them that they are at risk from heart disease because they are overweight, for example, many people know that this judgment is not necessarily specific to them—it is based on averages and demographics. So being a particular weight may not negatively affect a particular person's heart. Even if they do believe it to be specific to them they often do not know how to lose weight in their particular case. Individuals respond to foods in different ways, for example.

This reason for not following good advice can be addressed by testing each person's heart to see if their heart is healthy. With hard data many would take this advice seriously should their heart show signs of heart disease. Unfortunately, measuring heart health can be expensive and dangerous. A cardiac pressure-volume loop, for example, can be determined by placing a catheter into the left ventricle of a person's heart. While this invasive testing can successfully measure the person's heart health through determining this cardiac pressure-volume loop, doing so results in the death of the person about 1% of the time. It is also expensive and involves significant trauma and stress on the person. Because of this, only persons that already appear to have heart disease are tested this way, which is generally too late to save them.

Another reason that people don't follow this good advice, or don't follow it for long enough to prevent heart disease, is because they do not see the benefit. When people take the advice of changing their diet and habits—which most people do not want to do—they often don't see the improvement. They may see that they have lost weight and perhaps that their blood pressure is lower, but these are not precise measures of heart health. Because of this, many people go back to their old habits only to later die of heart disease.

SUMMARY

This document describes noninvasive determination of functional states and trends for human physiological systems, such as cardiac health through relevant hemodynamics understood by pressure-volume loops. Various noninvasive health monitors can be used to sense a person's health. While these noninvasive health monitors may not be as accurate as an invasive intra-heart test, for example, they require little if any risk to the person and are simple and easy for the person to use. Further, the techniques described herein can determine trends in a person's cardiovascular health. With these trends, a person can know if the effort they are expending to improve their heart health is actually making a difference. Further, negative trends can be found that can spur people to improve their health or to get medical attention. By so doing, these techniques may save many people from dying of heart disease.

This summary is provided to introduce simplified concepts concerning the techniques, which are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices for noninvasive determination of cardiac pressure-volume loops and other functional states and trends are described with reference to the following drawings. The same numbers are used throughout the drawings to reference like features and components.

DETAILED DESCRIPTION

Overview

This document describes techniques using, and devices enabling, noninvasive determination of cardiac pressure-volume loops, as well as other functional states of other human physiological systems. Through use of these techniques and devices, health data for a person can be sensed and then used to determine the person's health or a health trend. Many people, on receiving this heath information, are more likely to act to maintain or improve their heath. Through wide application of these techniques, many thousands if not millions of lives can potentially be saved.

By way of one example, assume that a person has three noninvasive health-monitoring devices in her bathroom. These three are a mat in front of her bathroom sink, a toilet-seat sensor, and a mirror over her bathroom sink. The mat measures her body's electrical behavior to provide an electrocardiogram. The toilet-seat sensor is capable of measuring a pulse-wave velocity of her blood sufficient to provide a cardiac pressure-volume loop. The mirror over her sink has sensors, such as a camera, that are capable measuring skin color variations, which can indicate differential blood volume to provide a photo-plethysmogram. Note that this person does not have to do anything outside of her normal course of life—simply washing her face while standing on the mat, looking into the mirror, and using the toilet provide opportunities for these three devices to sense her cardiovascular health. Assume also that, over the course of a new diet and exercise routine, that the techniques, using data from these devices, determines that her heart's stroke volume (and important measure of heart health) has improved 6% in four weeks. With this positive feedback, this person may continue her diet and exercise routine, thereby likely reducing the chances that she will die of heart disease.

This is but one simple example of ways in which noninvasive determination of cardiac pressure-volume loops for a human cardiovascular system or functional states of other physiological systems can be performed, other examples and details are provided below. This document now turns to an example environment, after which example noninvasive health-monitoring devices and methods, as well as cardiovascular functional states and trends and an example computing system are described.

Example Environment

Figure 1:
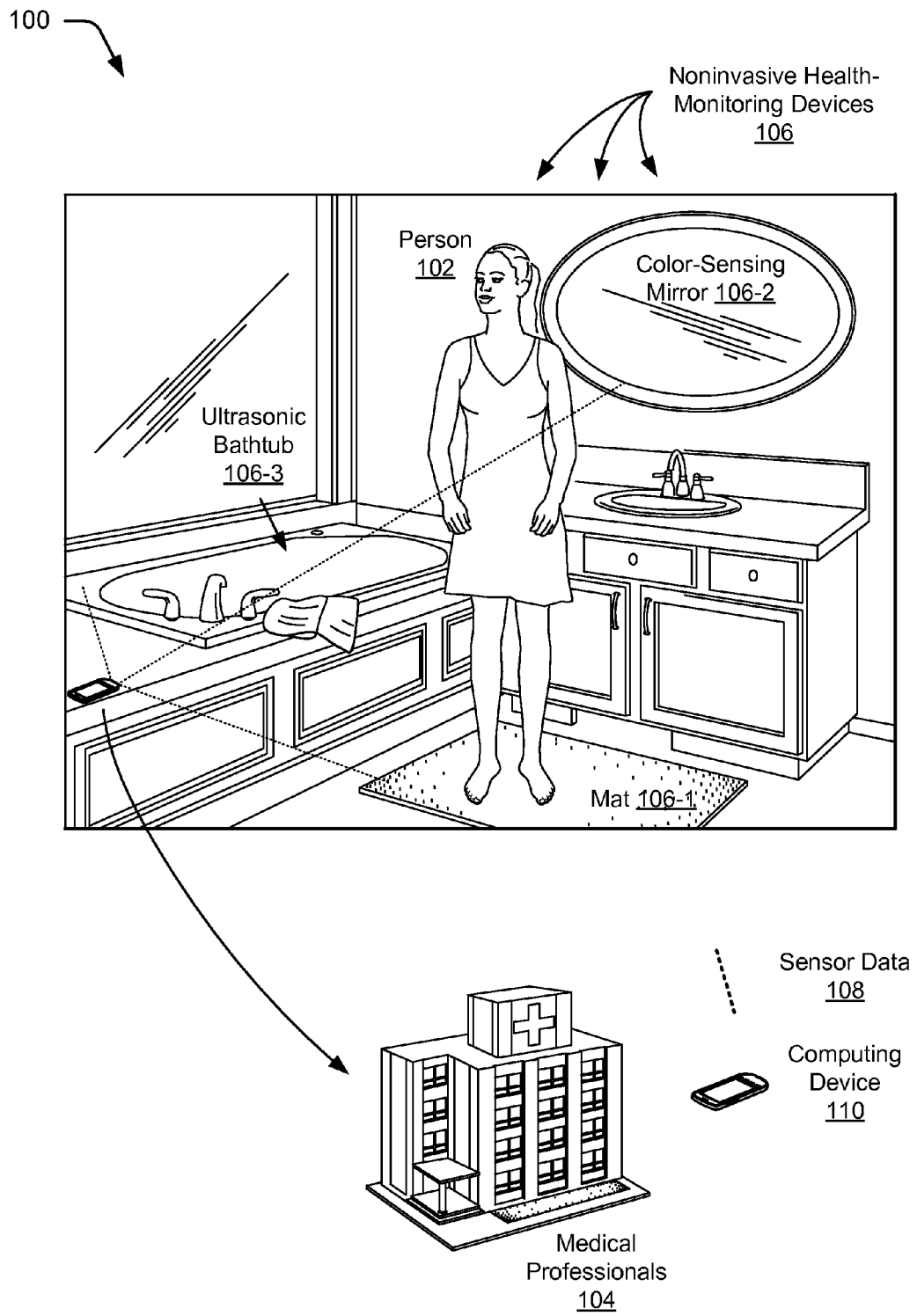
FIG. 1 illustrates an example environment in which the techniques can be implemented.

FIG. 1 is an illustration of an example environment 100 in which noninvasive determination of cardiac pressure-volume loops for a human cardiovascular system or functional states of other physiological systems can be employed. Environment 100 illustrates a person 102 that is the subject of the health monitoring, as well as a medical professional 104 that, in some cases, will receive results of the health monitoring. This example employs noninvasive health-monitoring devices 106 (devices 106), including pressure and electrical-sensing mat 106-1 (mat 106-1), color-sensing mirror 106-2, and ultrasonic bathtub 106-3. Other example noninvasive health-monitoring devices 106 are illustrated in later figures.

Sensor data 108 is provided by each of devices 106 to some computing device, such as a computing device 110, which then performs some or all of the techniques, or passes that sensor data to some other computing device, such as a remote server through a communication network (not shown).

As shown with this example environment 100, a sensing milieu (e.g., devices 106 in person 102's bathroom) in which a person lives can be used that, through a combination of various sensing modalities, is capable of determining a functional state of a human physiological system, such as a cardiovascular system. This sensing milieu is capable of determining this functional state, or at the least trends in this functional state, without actually measuring that system through an invasive test. This sensing milieu senses various conditions of the person, which can then be correlated, aggregated, and so forth to determine the functional state of that physiological system. While the above examples address the cardiovascular system, other physiological systems may also be sensed, including the nervous, endocrine, muscular, skeletal, and integumentary systems.

A functional state of a system includes sufficient data from which to determine a current health or a longer-term trend for the system. Sensor data indicating that a person's walking gate is irregular and that the person's spine includes various subluxations, can be analyzed to find a functional state for a skeletal system indicating that the person's left knee has a reduced range of movement.

By way of another example, sensor data may indicate a person's blood pressure at a particular instance in time. This blood pressure alone, however, is unlikely to be sufficient to determine a current health unless that blood pressure is within extreme ranges for human cardiovascular systems. This blood pressure cannot on its own show a trend. Blood pressure can indicate a functional state of a cardiovascular system when analyzed over time, however. Assume that blood pressure is measured over a week. These blood pressures can be normalized based on corresponding heart rates and activities in which the blood pressure were measured, such as a heart rate of 130 beats per minute for one blood pressure reading and being in a deep sleep for another blood pressure reading. By analyzing and correlating blood pressure readings with other readings and over some period of time, a functional state determined based on blood pressure can be found. Detailed functional states represented as pressure-volume loops are described in FIGS. 9-17 below.

Figure 2:
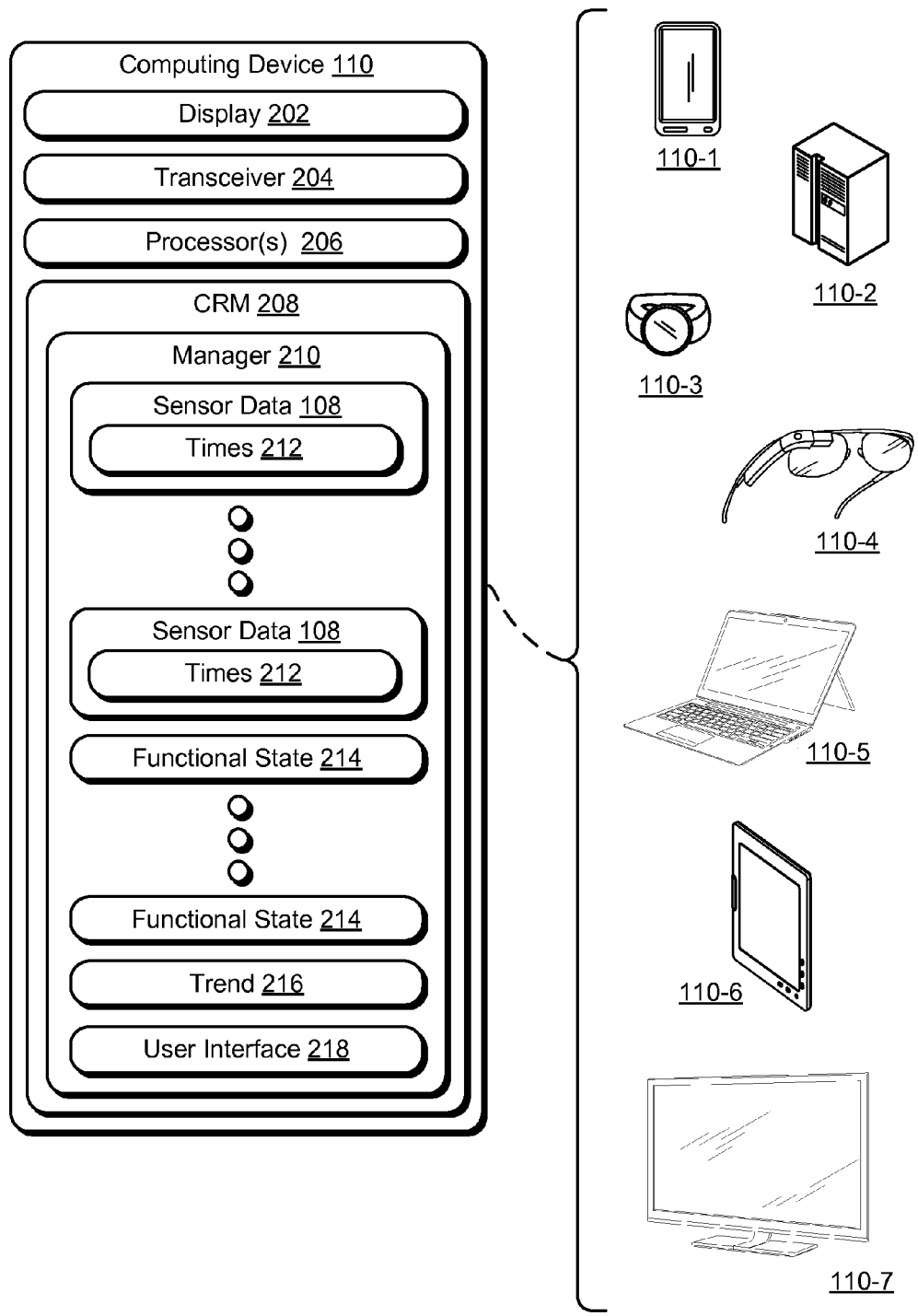
FIG. 2 illustrates an example computing device of FIG. 1.

With regard to the example computing device 110 of FIG. 1, consider a detailed illustration in FIG. 2. Computing device 110 can be one or a combination of various devices, here illustrated with seven examples: a smartphone 110-1, a server 110-2, a computing watch 110-3, computing spectacles 110-4, a laptop 110-5, a tablet computer 110-6, and a desktop 110-7, though other computing devices and systems, such as a netbook or set-top box may also be used. As noted above, in some embodiments the techniques operate, in whole or in part, through a remote device such as server 110-2. In such cases, some computing can be forgone locally, e.g., through a communication device having limited computing operations or even directly from devices 106 to server 110-2.

Computing device 110 includes or is able to communicate with a display 202 (six are shown in FIG. 2), a transceiver 204, one or more processors 206, and computer-readable storage media 208 (CRM 208). Transceiver 204 is capable of sending and receiving data directly or through a communication network, such as sensor data 108 from devices 106 through a local area, wide area, personal area, cellular, or near-field network.

CRM 208 includes manager 210, which includes or has access to sensor data 108, which may include sensor data 108 from multiple devices 106 and having different modalities. This sensor data 108 can be associated with particular times 212, such that simultaneously received sensor data 108 can be correlated to determine functional states 214 of human physiological systems and trends 216 can be determined based on sensor data 108 changing over time. CRM 108 also includes or has access to a user interface 218, that, while not required, can be used to present determined trends, health, and medical advice to person 102.

Generally, manager 210 is capable of determining, based on sensor data 108, a functional state of a physiological system of a person, such as person 102 of FIG. 1. With this functional state, manager 210 may alert person 102 or medical professionals 104 of a negative health condition needing immediate care, for example. Manager 210 is also configured to determine trends based on the current functional state and prior-determined functional states, such as those determined at prior times.

Figure 3:
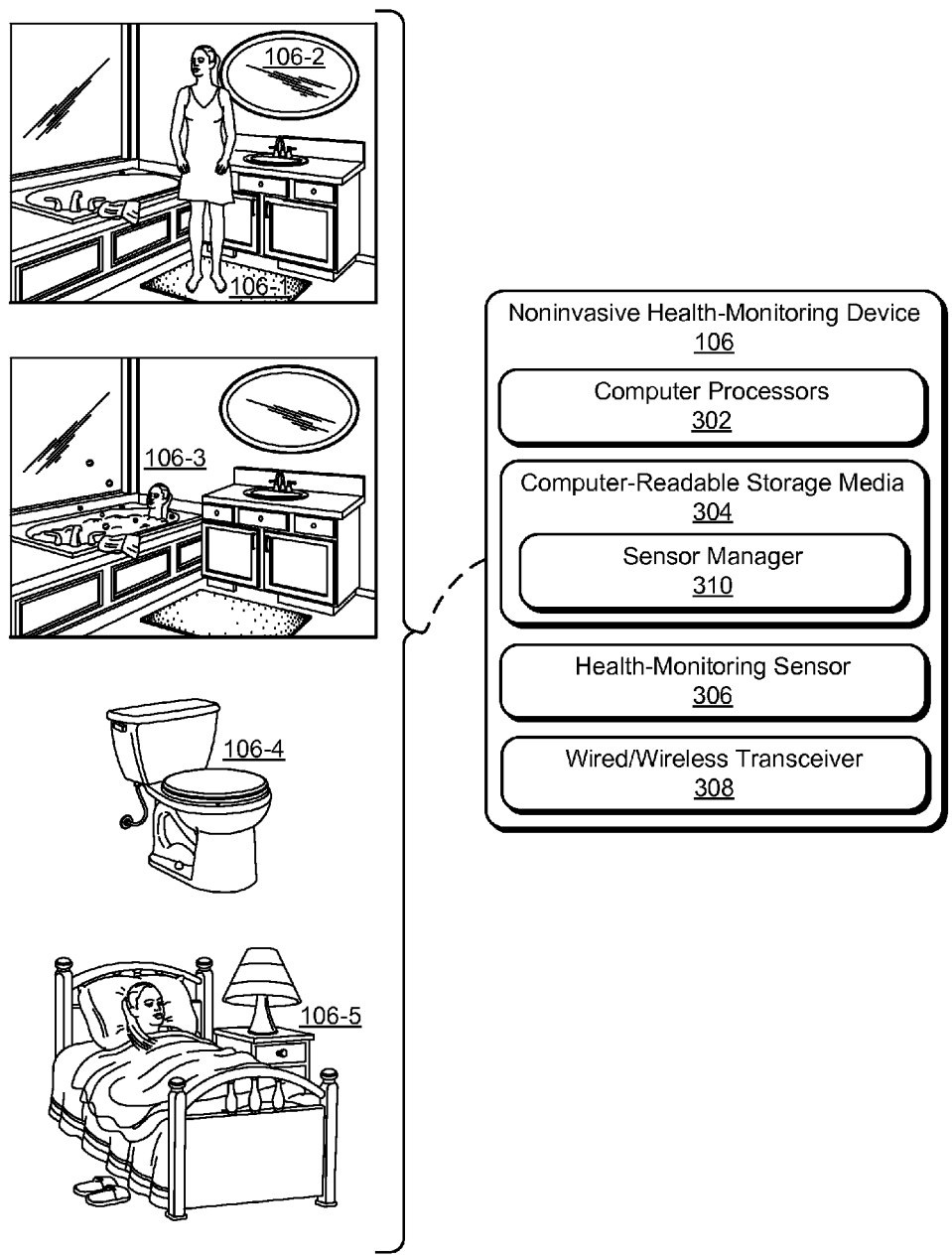
FIG. 3 illustrates an example noninvasive health-monitoring device of FIG. 1.

With regard to noninvasive health-monitoring devices 106, three examples of which are shown in FIG. 1, consider a detailed illustration in FIG. 3. Noninvasive health-monitoring device 106 can be one or a combination of various devices, here illustrated with five examples: pressure and electrical-sensing mat 106-1 (mat 106-1), color-sensing mirror 106-2, ultrasonic bathtub 106-3, pressure-sensing toilet seat 106-4 (toilet 106-4), and radar-field device 106-5. Some of these devices, while being noninvasive, actively sense the patient's health, such as through sending out sound waves (e.g., ultrasonic bathtub 106-3), electromagnetic waves, electrical signals, and millimeter and similar radiation (e.g., radar-field device 106-5). Others of these devices can be fully passive, such as sensing pressure of person 102's blood through toilet 106-4.

In more detail, pressure and electrical-sensing mat 106-1 is configured to sense a pulse-wave velocity of person 102's blood. This pulse-wave velocity can be used to determine a pressure-volume loop, described later herein. This pulse-wave velocity is a measure of a person's artery health. In healthy arteries the pulse-wave velocity is low due to the elasticity of the arteries but, as they harden and narrow, the pulse-wave velocity rises. While a particular pulse-wave velocity as a snap shot in time may or may not accurately indicate cardiovascular health (e.g., a one-time test at a doctor's office), a change in this pulse-wave velocity (that is, a trend), can be an accurate measure of a change in person 102's cardiovascular health. If a positive trend, this can reinforce person 102's healthy habits and, if negative, encourage changes to be made.

Mat 106-1 may also measure a heart's electrical conduction system through electrical impulses generated by the polarization and depolarization of cardiac tissue, and then translates this to a waveform (alone or by another entity). Measurements alone, or trends over time, can indicate hypercalcemia, hypocalcemia, hyperkalemia, hypokalemia, coronary ischemia, or myocardial infarction (i.e., a heart attack). Note also that functional states or trends found through data sensed by devices 106, as will be discussed later, can determine a negative heart or other system condition sooner than may otherwise be found, thereby catching a decline in health soon enough to counter it.

Color-sensing mirror 106-2 is configured to record colors in a person's skin sufficient to determine a photo-plethysmogram. A plethysmogram measures variations in a size or color of an organ, limb, or other human part from changes in an amount of blood present in or passing through it. These colors and color variations in a person's skin can show heart rate and efficiency. Further, color-sensing mirror 106-2 may also radiate, at low and safe levels, person 102 and sense the backscatter from the radiation, thereby determining more robustly or accurately person 102's integumentary, muscular, or cardiovascular system health and efficiency.

Ultrasonic bathtub 106-3 is configured to generate high-frequency sound waves and to evaluate an echo from those waves. This echo is received at one or more sensors and the time interval between sending and receiving can be measured. These echoes enable analysis of internal body structures. In some cases, acoustic impedance of a two-dimensional cross-section of tissue can be measured, which can measure current heath or a health trend of the measured tissue. Blood flow, tissue movement, blood location, and three-dimensional measurements of structures can also be made. Passive (no sound waves generated, just receiving sensors) can be used, though accuracy and robust measurements are more difficult to achieve.

Pressure-sensing toilet seat 106-4 is configured to sense pulse-wave velocity as noted for mat 106-1 above, but can also study the heart on different conditions, such as measuring cardiovascular health through bowel movements, which are similar to a Valsalva maneuver (named after surgeon Antonio Maria Valsalva, 1666-1723) used by some cardiologist to measure heart reactivity.

Radar-field device 106-5 is configured to reflect radiation from human tissue to measure skin temperature and perspiration, heart rate, and skeletal movement, to name just three examples. Radar-field device 106-5 includes a microwave radio element that provides a radar field configured to reflect from human tissue and penetrate non-human material, such as through continuously modulated radiation, ultra-wideband radiation, or sub-millimeter-frequency radiation. These reflections can be received by an antenna element and then processed by a signal processor to provide sensor data 108. This radar field can reflect from human tissue, such as skin, bone, or heart muscle. Assume, for example, that person 102 is asleep and radar-field device 106-5 is integral with a lamp on her nightstand. Normally people move around a lot and thus sensor data can be unreliable or noisy. In the case of sleep, however, radar-field device 106-5 measures person 102's chest deflections to record respiration rate. These chest deflections includes wiggles or perturbations caused by person 102's heartbeat and thus a heart rate can also be calculated.

These examples show some ways in which the techniques can provide substantially more-valuable (or at least different) data of a person's health than those provided in a medical office or hospital. As noted, conventional health monitoring is often performed at a hospital or medical practitioner's office. Health monitoring at a hospital or office, however, cannot monitor a person during their normal course of life. This can be a serious limitation because a snapshot captured at a hospital or office may not accurately reflect the person's health. This can be due to the testing being of a short duration or due to the testing being in an artificial environment.

Returning to noninvasive health-monitoring device 106 generally, device 106 may having various computing capabilities, though it may instead be a low-capability device having little or no computing capability. Here device 106 includes one or more computer processors 302, computer-readable storage media 304, a health-monitoring sensor 306, a wired or wireless transceiver 308 capable of receiving and transmitting information (e.g., to computing device 110). Health monitoring sensor 306 may include one of the many sensors described herein. Computer-readable storage media 304 includes sensor manager 310, which is capable of processing sensor data and recording and transmitting sensor data for a health-monitoring act.

These and other capabilities, as well as ways in which entities of FIGS. 1-3 act and interact, are set forth in greater detail below. These entities may be further divided, combined, and so on. The environment 100 of FIG. 1 and the detailed illustrations of FIGS. 2 and 3 illustrate some of many possible environments capable of employing the described techniques.

Example Methods

Figure 4:
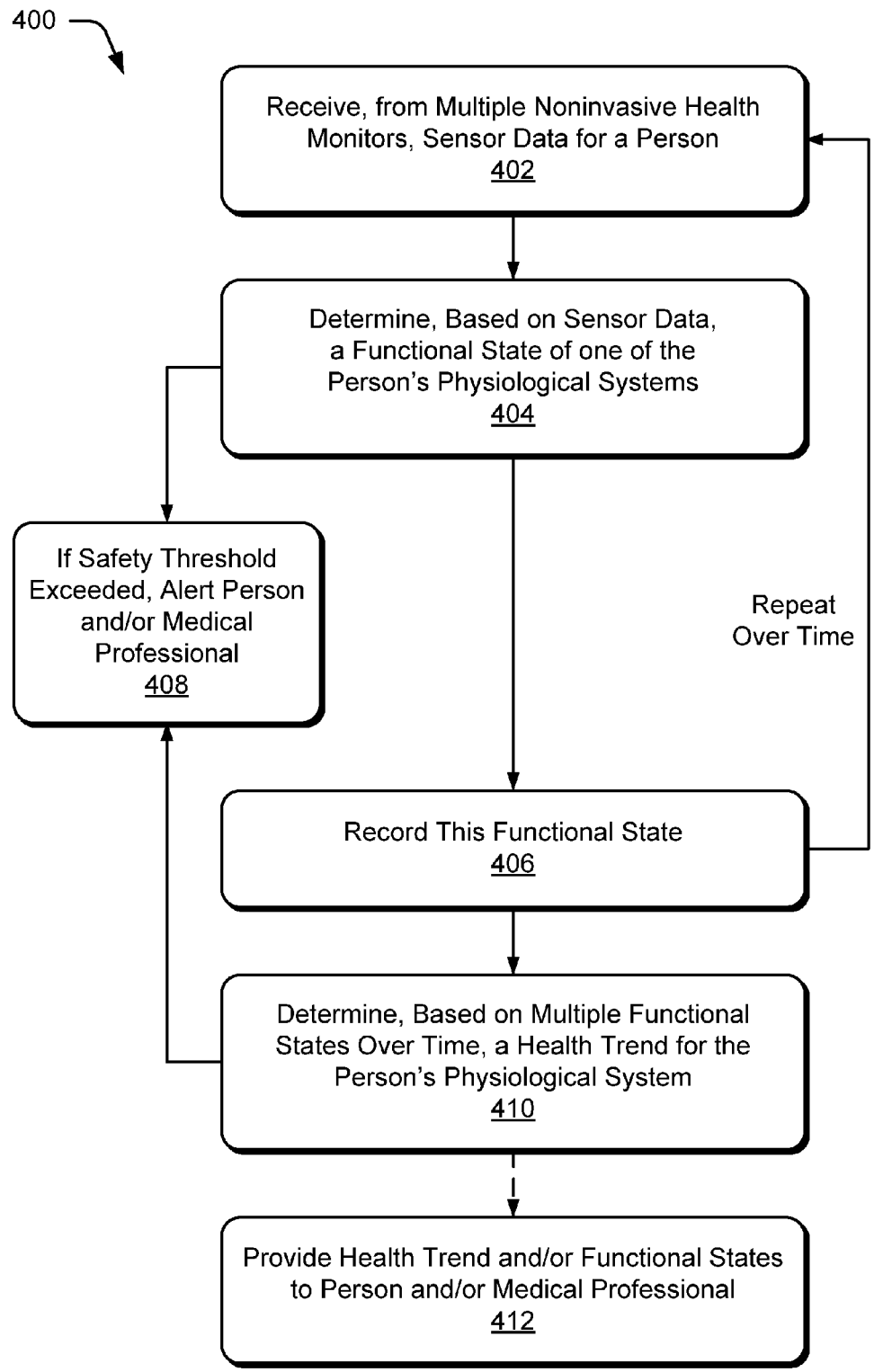
FIG. 4 illustrates a method for noninvasive determination of functional states or trends for human physiological systems.
Figure 6:
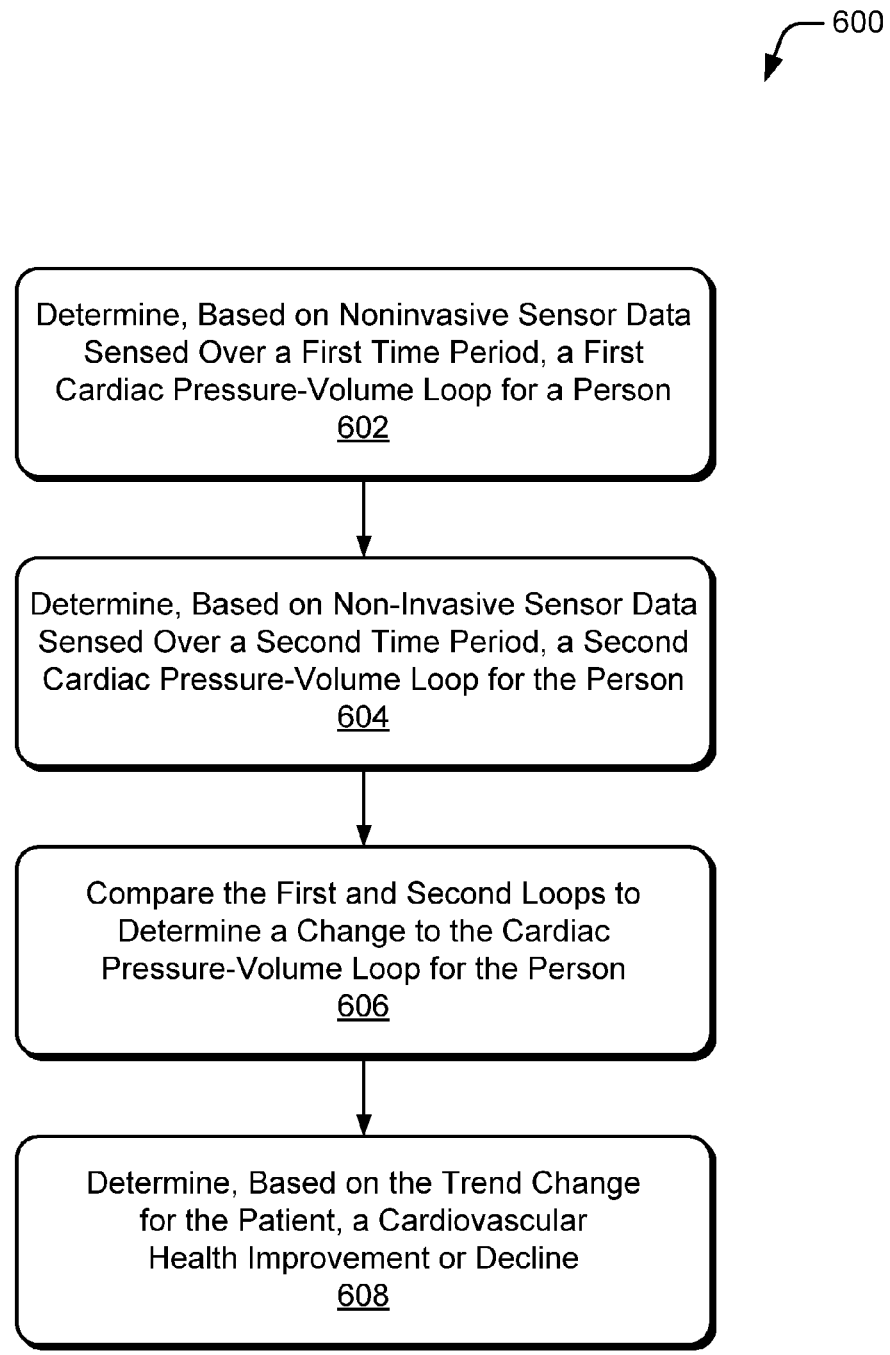
FIG. 6 illustrates a method to determine trends based on changes in cardiac pressure-volume loops.

FIGS. 4 and 6 depict methods enabling or using noninvasive determination of cardiac pressure-volume loops. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIGS. 2 and 3, reference to which is made for example only. The techniques are not limited to performance by one entity or multiple entities operating on one device.

At 402, sensor data for a person is received from multiple noninvasive health monitors. As noted in part above, these noninvasive health monitors can include those having two or more different modalities by which to measure a physiological system, such as through reflected light, sound waves, electromagnetic sensing, radar, and fluid mechanics (e.g., pressure wave velocity measurements). Noninvasive health monitors sense a person's health without requiring the person being sensed to explicitly operate or actively interact with the monitoring device. Thus, a person need not put a thermometer in her mouth, attach a wired, heart rate sensor to his chest, or otherwise interrupt his or her daily routine for his or her health to be monitored. Sensor data from these one or more noninvasive health monitors can be recorded simultaneously or very nearly at a same time and be passively sensed or actively sensed, as noted above.

At 404, a functional state of one of the person's physiological systems is determined based on the sensor data. The health-monitoring devices may be of varying accuracy—some may be capable of sensing particular biological aspects accurately even compared to invasive sensing, while others can measure the physiological system but not accurately enough for a medical professional to be able to tell the persons health based on a single or short set of sensor data. This imperfect sensing, however, can be used to determine a person's health better in at least two ways. In a first, sensor data from multiple devices is correlated, aggregated, and so forth to, in total, better determine a functional state and thus a current health of the physiological system. In a second, the functional state may not be capable of indicating a current health, but a change in that functional state over time indicates a trend that does indicate a change in health. Consider, for example, a simple case where a person's respiration, heart rate, and skin temperature are measured and correlated (based on time sensed) when the person is in deep sleep. Based on one or two of these functional states, a medical professional may not be able to determine the person's health because people are different. Statistics and demographics and even data about the person's overall health and so forth may be sufficient to determine the person's health. A trend showing a change to a functional state over weeks, months, or years to the person's respiration, heart rate, and skin temperature can show that the person's heart has to work harder than before or is less effective, and so forth. Determining the functional state of the physiological system of the person can correlate sensor data from one the multiple noninvasive health monitors with sensor data from another of the multiple noninvasive health monitors through sub-second precision relating to an element of the physiological system.

Using the example of FIGS. 1-3, noninvasive health-monitoring devices 106 of FIGS. 3 and 1 sense, through health-monitoring sensor 308, various sensor data 108. This sensor data 108 is then transmitted to computing device 110 through wired/wireless transceiver 308. This transmitted sensor data 108 is received from ultrasonic bathtub 106-3, mat 106-1, and color-sensing mirror 106-2 at transceiver 204 of computing device 110. Manager 210 then correlates, aggregates, and analyzes this sensor data 108, often using times 212 in which various sensor data 108 is measured to determine functional state 214 and store that state.

At 406, this functional state is recorded. This can be recorded at a computing device local to or remote from the person, such as a computing device 110. Generally, this sensing and determining of functional states are repeated over time, following operation 406 to repeat operations 402, 404, and 406. In some cases, however, a functional state determined at 404 is determined to meet a danger threshold. In such cases, method 400 proceeds to operation 408.

At 408, the person or a medical professional associated with the person is alerted responsive to the functional state exceeding a safety threshold. This threshold can be as simple as a maximum blood pressure being too high, a heart rate being too rapid or irregular, or a low blood-oxygen level. This threshold can also be complicated or more difficult to determine, such as a person's heart showing an end-diastolic volume ejected out of a ventricle during a contraction being less than 0.55 (this is a measure of ejection fraction (EF) and low fractions can indicate a heart attack is imminent).

At 410 a health trend for the physiological system is determined based on the functional state and other, previously recorded functional states for the physiological system. As noted at operation 408, in some cases the techniques warn the person or a medical professional, as above for a functional state exceeding a safety threshold. Determined health trends can also exceed safety thresholds. In such a case method 400 proceeds to operation 408 rather than to 412. By way of example, assume that the person being measured weighs 200 lbs. at some point. That in and of itself may not indicate any problem. If that person's weight goes from 200, then to 205, and then to 210 over the course of one week that person may be in heart failure. This trend—gaining weight quickly—can indicate a failing heart. Alerting the person's medical professional may save his life because the physician may be able to intercede before a major heart attack.

At 412, the determined trend or functional states for the person are provided to the person or his associated medical professional. These trends and functional states can be provided after some number of measurements, various time periods elapsing (e.g., 30 days), and so forth. In some cases these are provided to manager 210 of computing device 110, which may then present these directly to the person, such as through a user interface on computing device 110. This can help motivate the person, thereby helping him or her stay on course for healthy changes or spur them to change his or her lifestyle.

While the above method 400 is described in the context of a cardiovascular system, which is still further detailed at method 600, the techniques are not limited to cardiovascular systems. Consider, for example, a skeletal system of an older woman. This physiological system, while not responsible for a large percentage of deaths, is responsible for many deaths and decreased health in the elderly. For this example assume that multiple radar-field devices 106-5, a camera associated with a gaming device, and an ultrasonic bathtub 106-3 are used to noninvasively monitor this woman's skeletal system.

Figure 5:
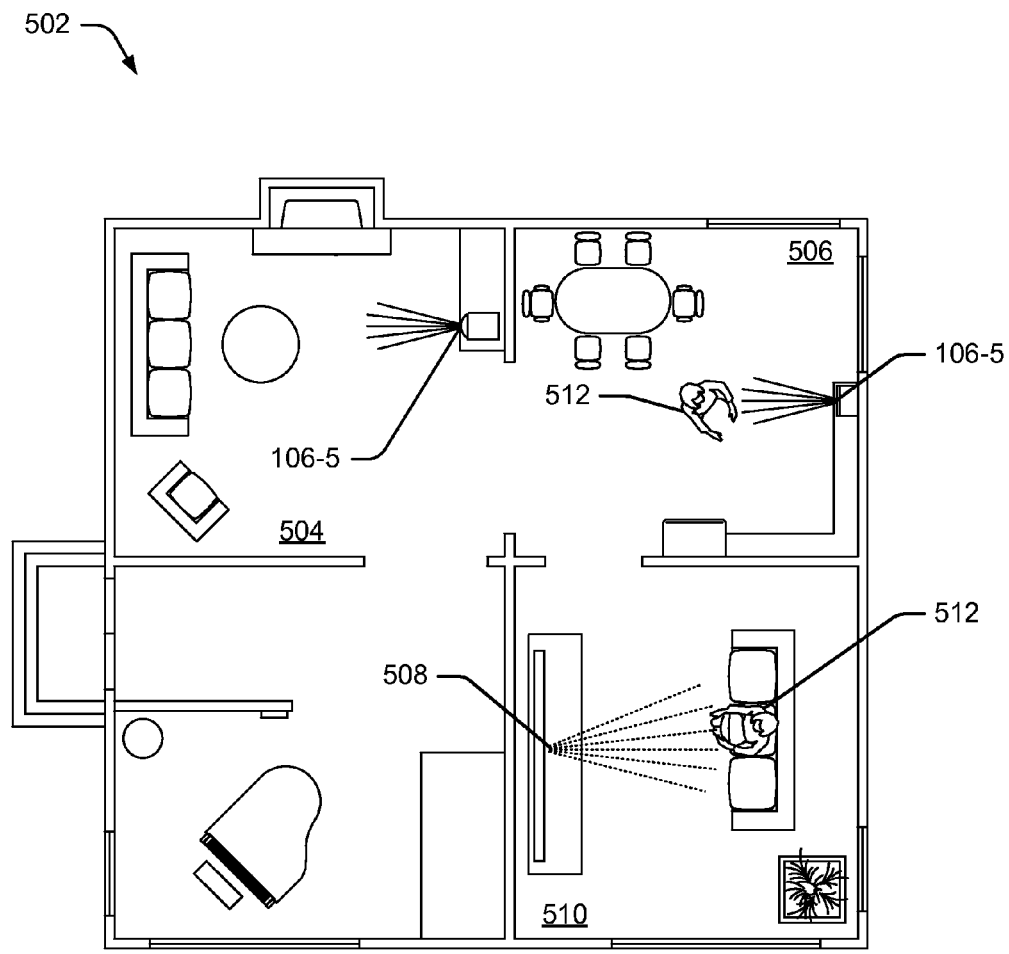
FIG. 5 illustrates a main floor of a house in which noninvasive health-monitoring devices are placed.

FIG. 5 illustrates a main floor of a house 502 in which two radar-field devices 106-5 are placed, one in living room 504 and another in kitchen 506. Camera 508 is in media room 510. Radar-field devices 106-5 can sense woman 512's height, skeletal shape, and body movement. Camera 508 can sense woman 512's body movement and height and, to a lesser extent, skeletal shape. Ultrasonic bathtub 106-3 can measure woman 512's bone density (not shown here, see FIG. 3). With these four measurements from various devices, manager 210 determines a functional state of woman 512's skeletal system. Trends can then be determined that may indicate osteoporosis or a failing knee or hip joint and thus medicine or lifestyle changes that the woman can undergo to slow this negative trend or avoid risk factors for these problems.

FIG. 6 depicts method 600, which describes manners in which to noninvasively determine a trend through differences in cardiac pressure-volume loops.

At 602, a first cardiac pressure-volume loop for a person is determined based on first noninvasive sensor data sensed over a first time period. This noninvasive sensor data includes the sensor data described above, such as pressure-wave velocity through mat 106-1 and toilet 106-4, of FIG. 1 or 3. This sensor data can include or be used to determine a ballisto-cardiogram reflecting pressure pulses, for example.

Figure 7:
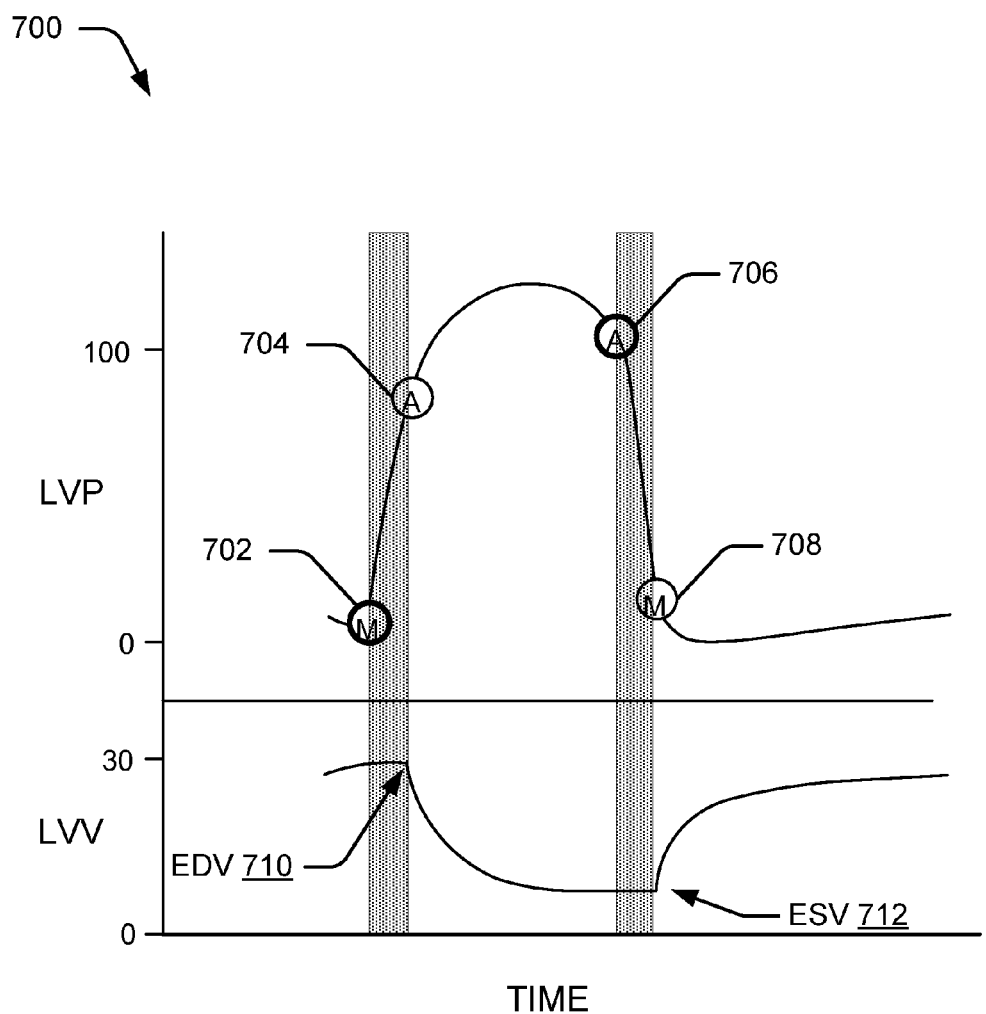
FIG. 7 illustrates a pressure-time diagram for a human heart.
Figure 8:
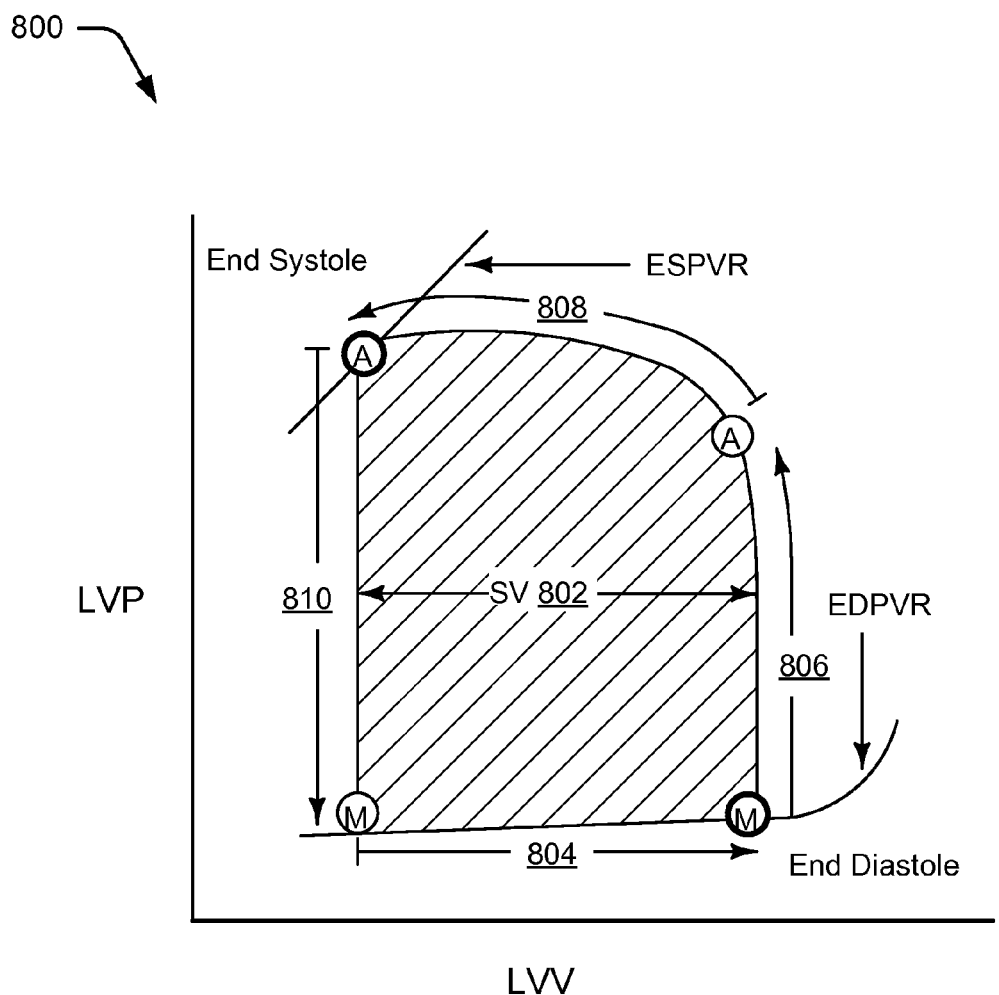
FIG. 8 illustrates a pressure-volume loop for the human heart of FIG. 7.

For context, consider FIGS. 7 and 8, which illustrate pressure-time diagram 700 and pressure-volume loop 800, respectively. Pressure-time diagram 700 shows two measurements, LVP (Left Ventricle Pressure) and LVV (Left Ventricle Volume) against a same time. While idealized, pressure-time diagram 700 shows a cardiac cycle for a heart at various actions, mitral valve closing 702, aortic valve opening 704, aortic valve closing 706, and mitral valve opening 708. EDV 710 shows End-Diastolic Volume and ESV 712 shows End-Systolic Volume with Stroke Volume (SV) (shown in FIG. 8) being EDV minus ESV.

Pressure-volume loop 800 shows LVP and LVV diagramed against each other for a single cardiac cycle. These diagrams show hemodynamic parameters useful in determining heart health, including stroke volume 802, diastolic filling 804, isovolumic contraction 806, ejection 808, and isovolumic relaxation 810. Pressure-volume loops are a useful visual representation of a heart's function, and therefore the cardiac health of the person, as are changes in a heart's pressure-volume loop, which is described and illustrated later below.

At 604, a second cardiac pressure-volume loop for the person is determined based on second noninvasive sensor data sensed over a second time period. This is based on second data as described above. This second cardiac pressure-volume loop, similar to the first loop above, may or may not be precise in terms of exact pressure or volume units in the heart. The trend between two loops measured in a similar way, however, can be accurate enough to show a change in cardiac health.

At 606, a change between the first and second cardiac pressure-volume loops for the person are determined by comparing the first and second loops. Numerous examples of some of the many changes that can be measured, and the corresponding health trends, are described following operation 608 below.

At 608 a trend for the patient's cardiovascular health is determined based on changes between these first and second loops. This trend can indicate a health improvement, decline, or no change, as noted below.

Figure 9:
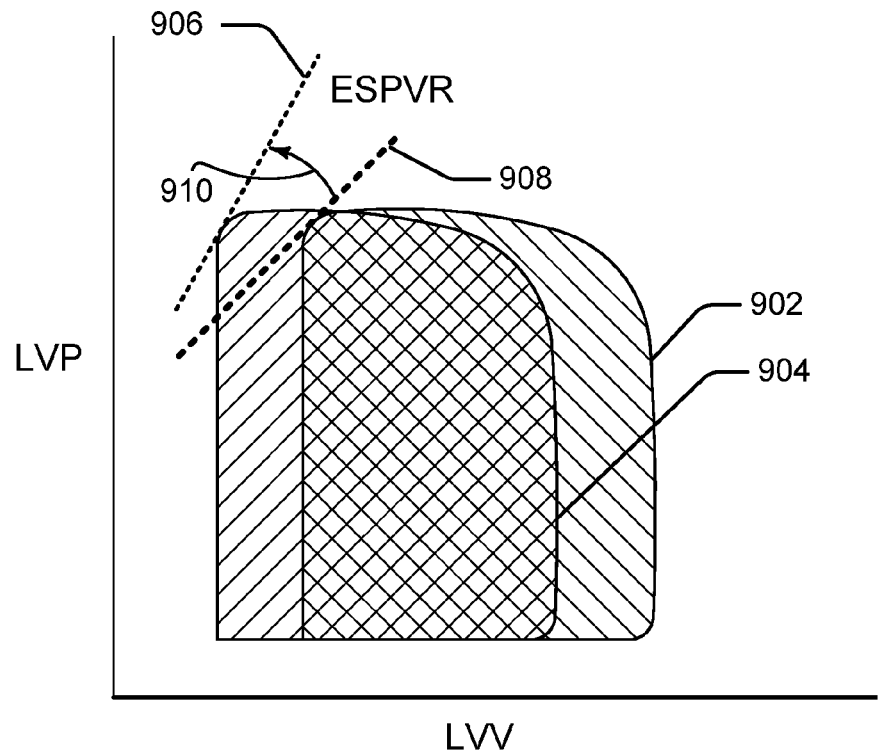
FIG. 9 illustrates pressure-volume loops showing increased inotropy.

FIG. 9 illustrates pressure-volume diagram 900 showing two loops, a change between them, and a corresponding trend. The trend here indicates increased inotropy, which is shown by an increased steepness of a second end-systolic pressure volume relationship (ESPVR) 906 for second loop 904 versus a first end-systolic pressure volume relationship (ESVPR) 908 for first loop 902. As can be readily seen, the exact measure of pressure and volume for the first and second loops 902 and 904 are not required to show this trend of increased steepness (shown at trend arrow 910), and thus the health condition it represents.

Figure 10:
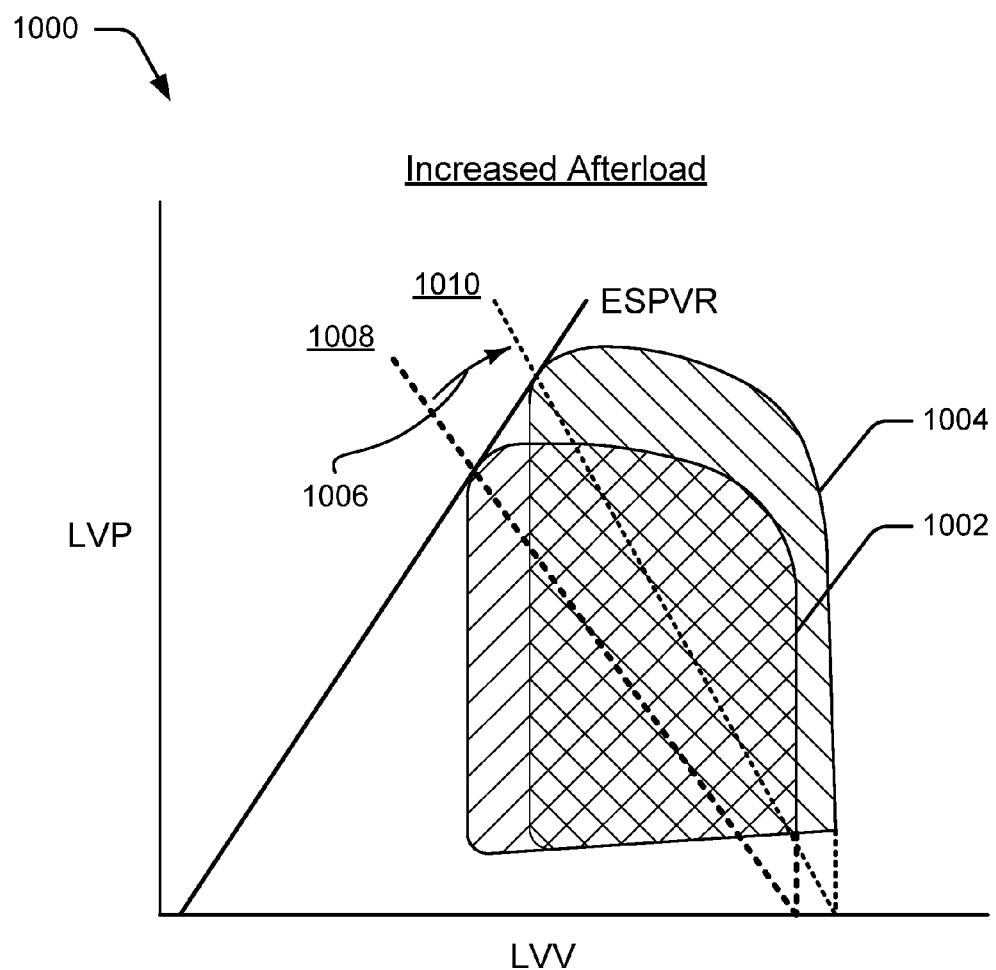
FIG. 10 illustrates pressure-volume loops showing increased afterload.

FIG. 10 illustrates an increased afterload diagram 1000. This diagram 1000 illustrates a first cardiac pressure-volume loop (first loop) 1002 along with a second cardiac pressure-volume loop (second loop) 1004, where the difference between the first and second loop show a trend 1006 of decreased arterial elasticity (or increased stiffness) from arterial elasticity 1008 of first loop 1002 to second arterial elasticity 1010 of second loop 1004. Decreased arterial elasticity is usually an indicator of declining cardiac health.

Figure 11:
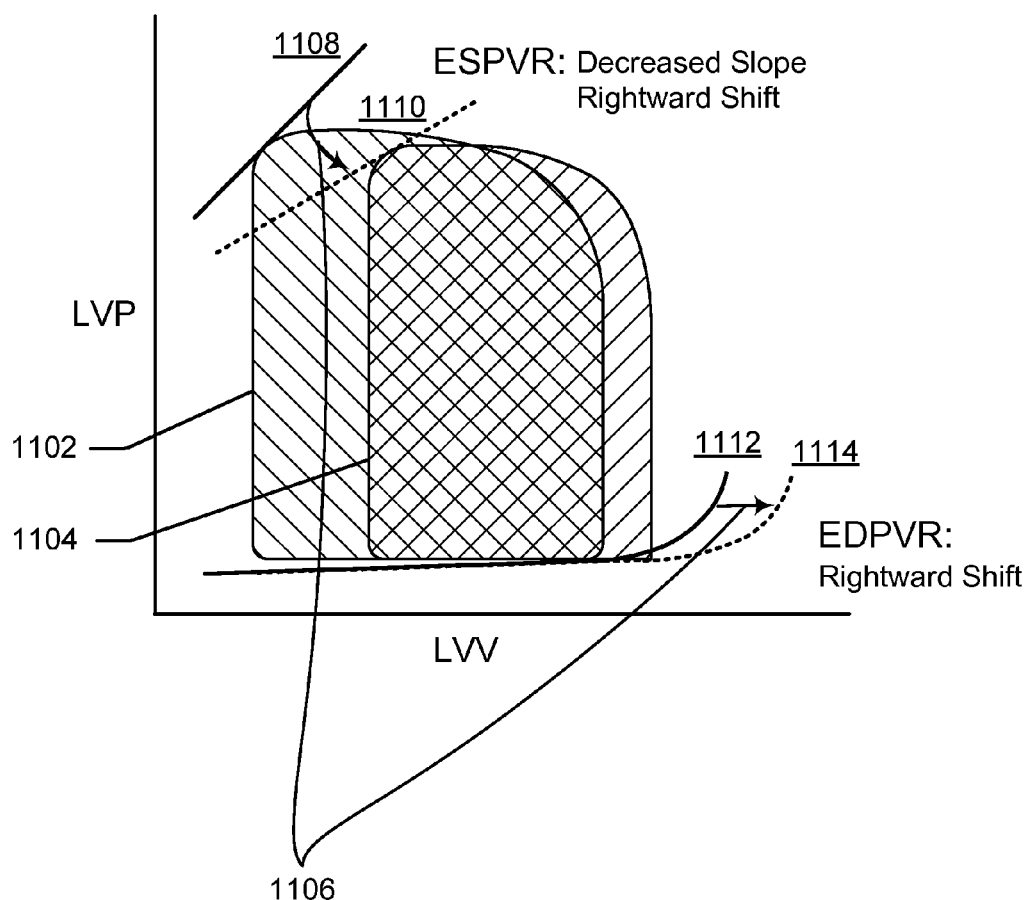
FIG. 11 illustrates pressure-volume loops showing dilated cardiomyopathy.

FIG. 11 illustrates a dilated cardiomyopathy diagram 1100. This diagram 1100 illustrates a first cardiac pressure-volume loop (first loop) 1102 along with a second cardiac pressure-volume loop (second loop) 1104 where a trend 1106 between the first and second loop shows a rightward shift from EDPVR 1108 of first loop 1102 to EDPVR 1110 of second loop 1104, as well as a rightward shift with a downward slope of ESPVR 1112 of first loop 1102 to ESPVR 1114 of second loop 1104. This trend (the shifts noted) indicate a ventricle becoming dilated without a compensating thickening of the ventricle wall. Because of this, the left ventricle is unable to pump enough blood, which can be fatal. Caught early, however, this trend may be reversible.

Figure 12:
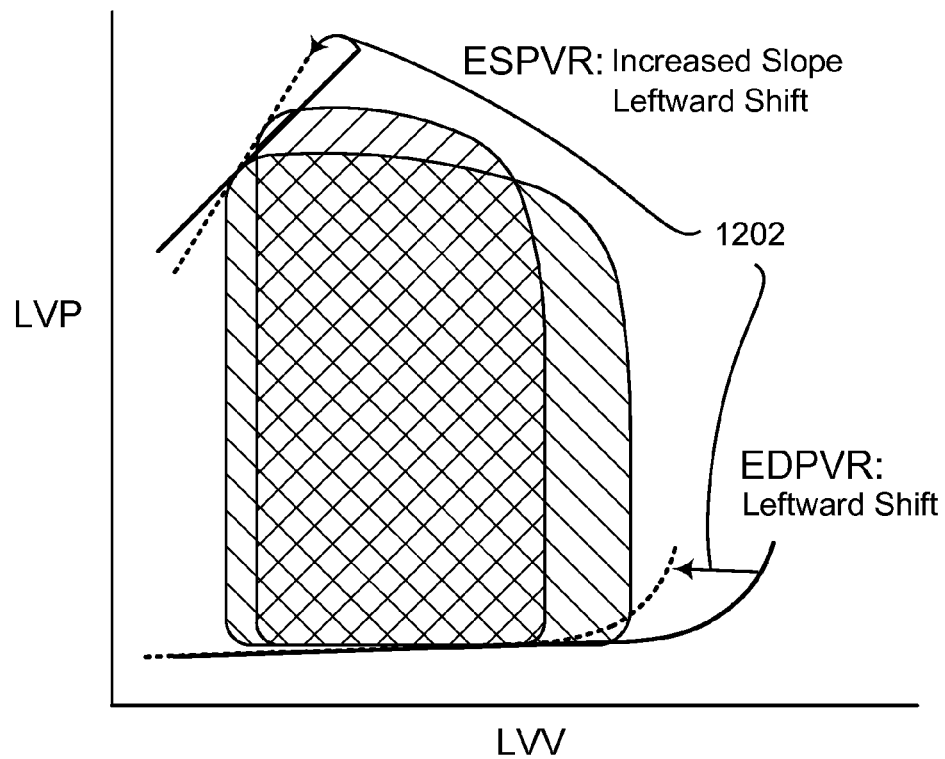
FIG. 12 illustrates pressure-volume loops showing left ventricular hypertrophy.
Figure 13:
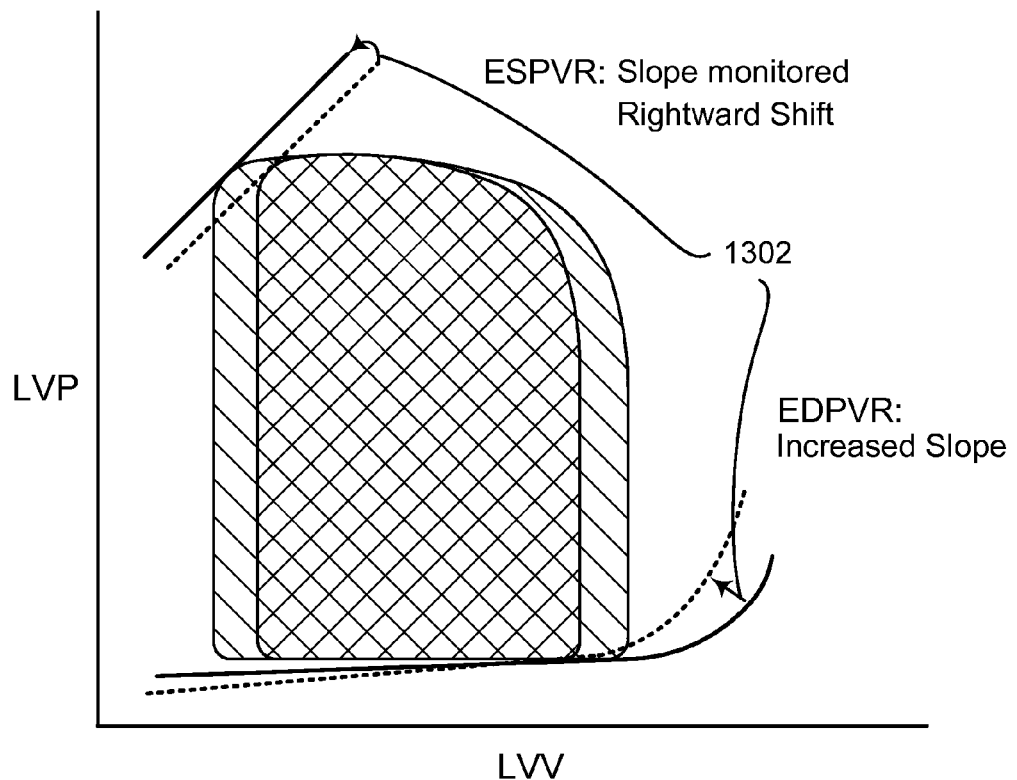
FIG. 13 illustrates pressure-volume loops showing restrictive cardiomyopathy.
Figure 14:
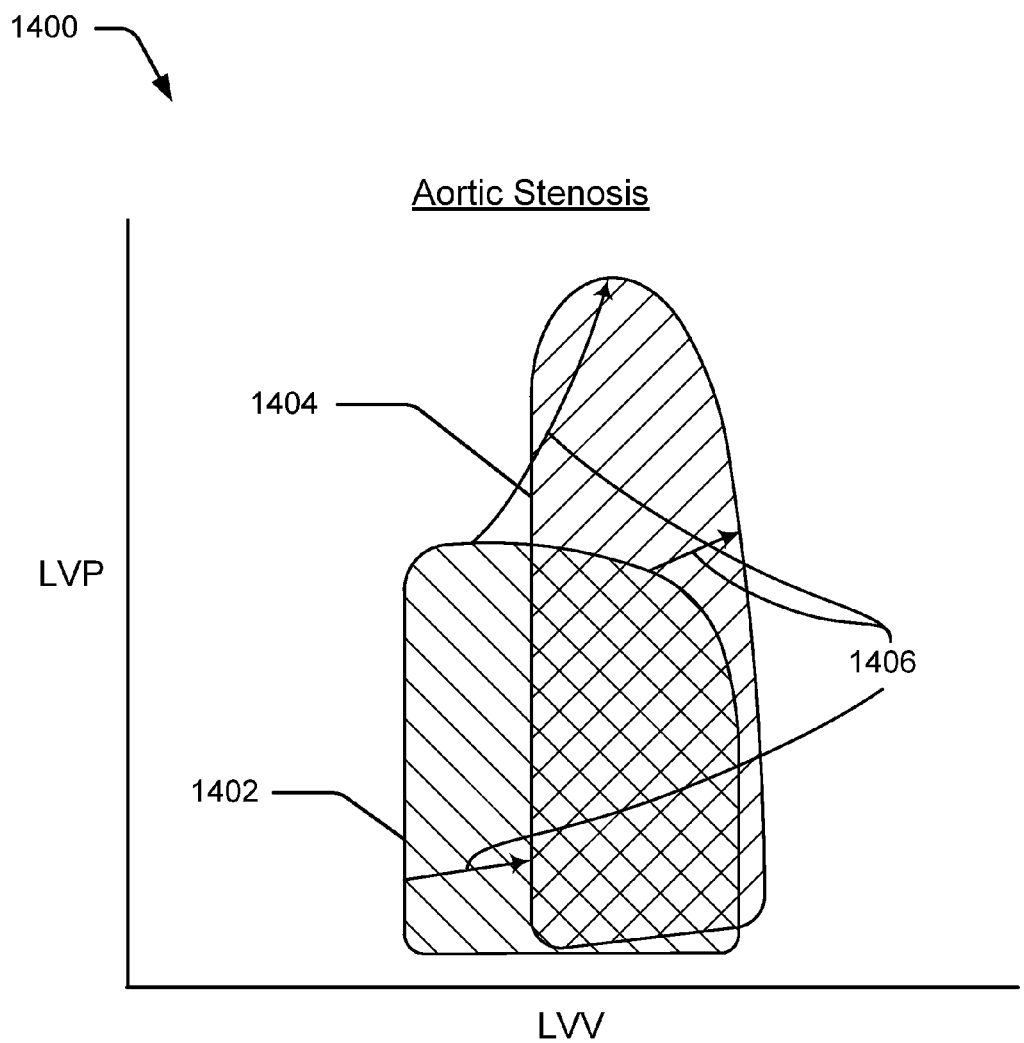
FIG. 14 illustrates pressure-volume loops showing aortic stenosis.
Figure 15:
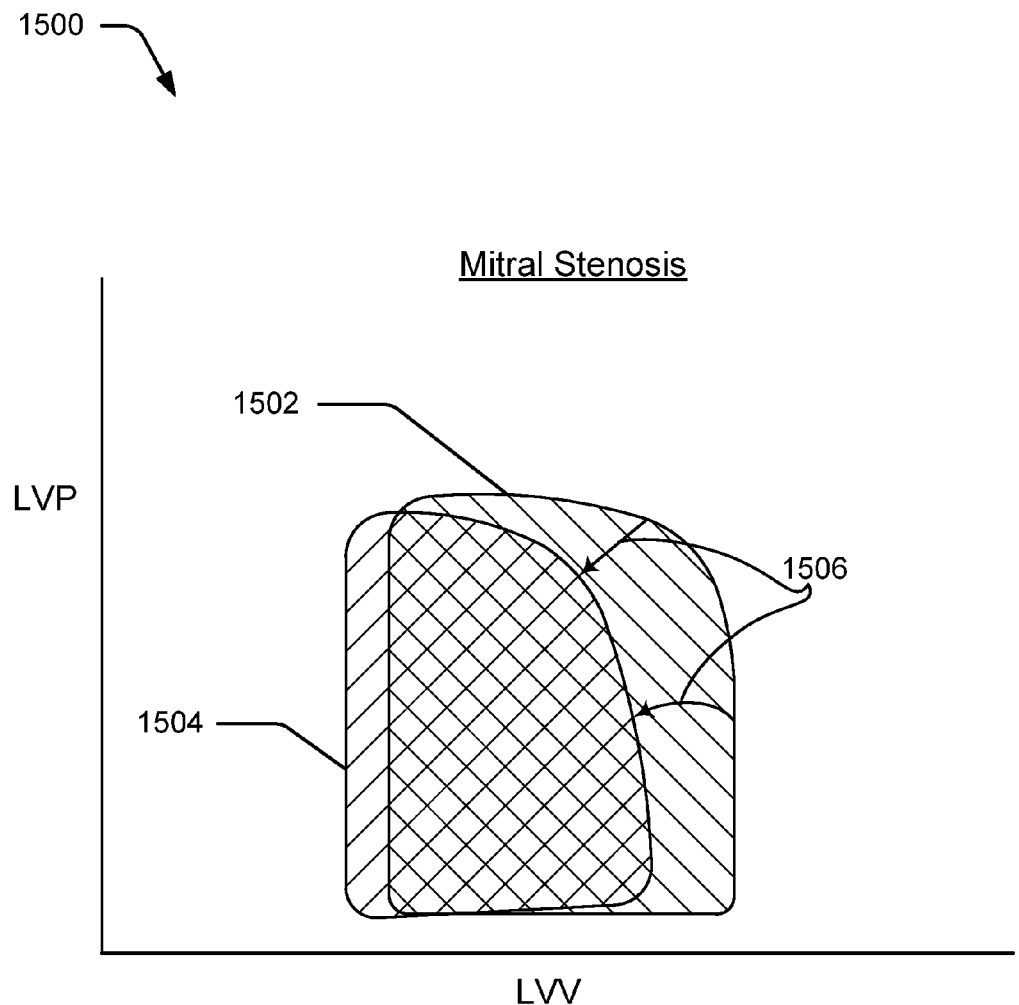
FIG. 15 illustrates pressure-volume loops showing mitral stenosis.

In addition to these three trends shown with cardiac pressure loops, there are also many others, such as left ventricular hypertrophy, shown in FIG. 12 at 1200 with trend 1202, and restrictive cardiomyopathy, shown in FIG. 13 at 1300 with trend 1302. There are also valve diseases that can be shown through trends for pressure-volume loops, including aortic stenosis, illustrated at diagram 1400 in FIG. 14 (first loop 1402 showing a healthy valve and second loop 1404 with aortic stenosis, trend 1406 shown with arrows indicating change in shape of the loops), and mitral stenosis illustrated at diagram 1500 in FIG. 15 (first loop 1502 showing a healthy valve and second loop 1504 with mitral stenosis, trend 1506 shown with arrows indicating change in shape of the loops).

Figure 16:
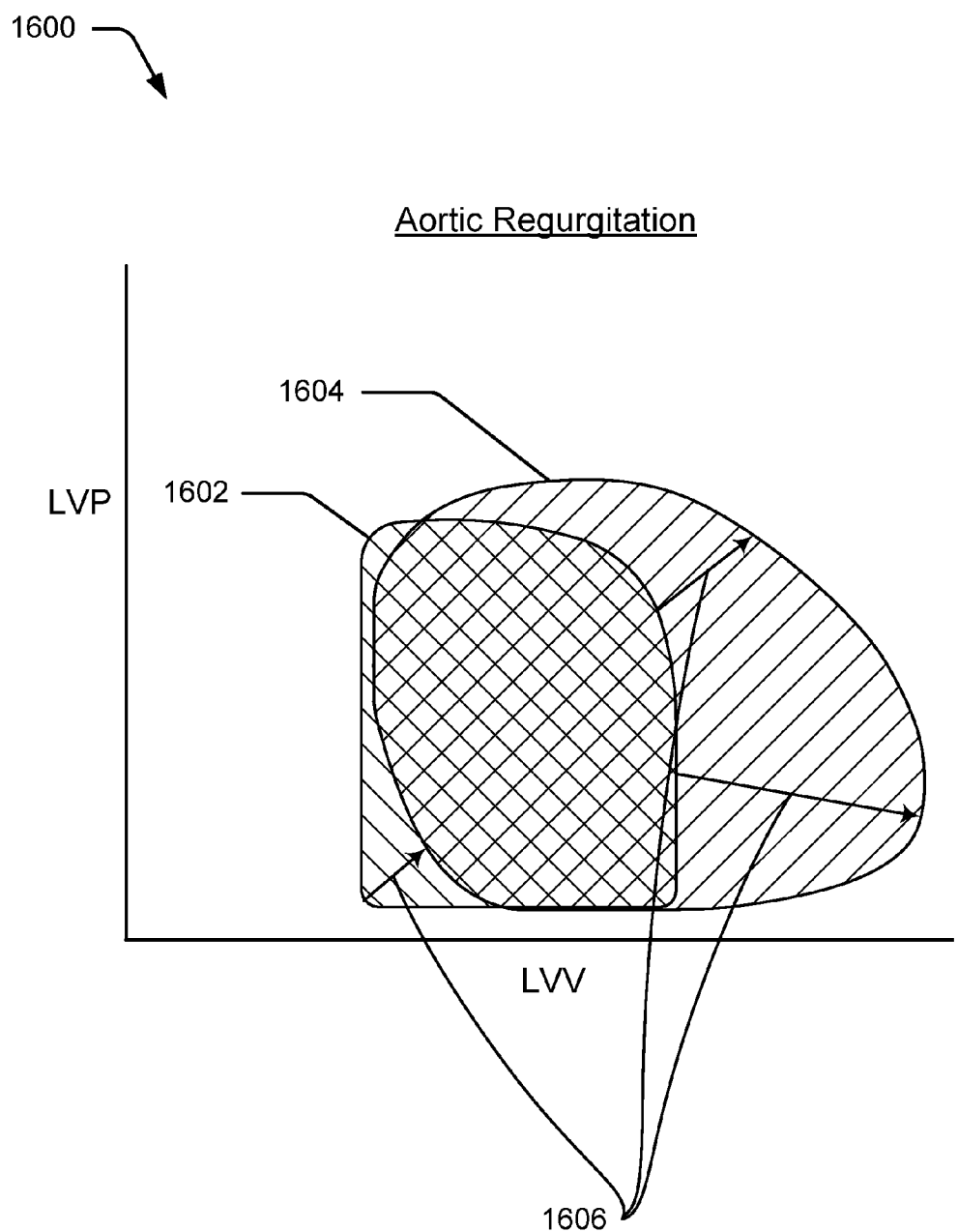
FIG. 16 illustrates pressure-volume loops showing aortic regurgitation.
Figure 17:
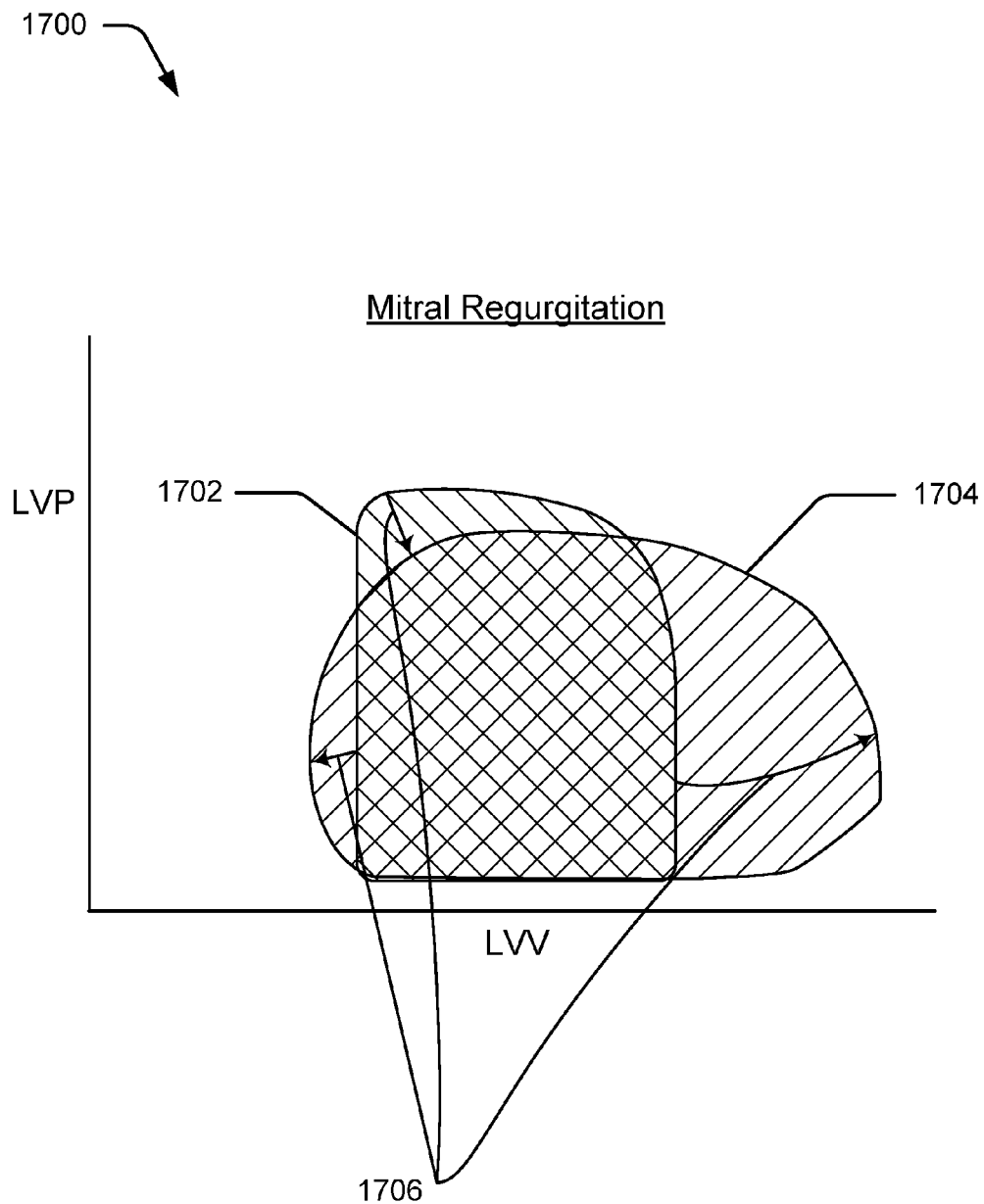
FIG. 17 illustrates pressure-volume loops showing mitral regurgitation.

Two forms of regurgitation can also be shown through changes to cardiac pressure-volume loops, aortic regurgitation shown at diagram 1600 of FIG. 16 (first loop 1602 being a healthy pressure-volume loop and second loop 1604 with aortic regurgitation, trend 1606 shown with arrows indicating change in shape of the loops), and mitral regurgitation shown at diagram 1700 of FIG. 17 (first loop 1702 being a healthy pressure-volume loop and second loop 1704 with mitral regurgitation, trend 1706 shown with arrows indicating change in shape of the loops). These diagrams show some of the many trends that the techniques can detect.

The preceding discussion describes methods relating to noninvasive determination of cardiac pressure-volume loops for a human cardiovascular system or functional states of other physiological systems. Aspects of these methods may be implemented in hardware (e.g., fixed logic circuitry), firmware, software, manual processing, or any combination thereof. These techniques may be embodied on one or more of the entities shown in FIGS. 1-3, 5, and 18 (computing system 1800 is described in FIG. 18 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 18:
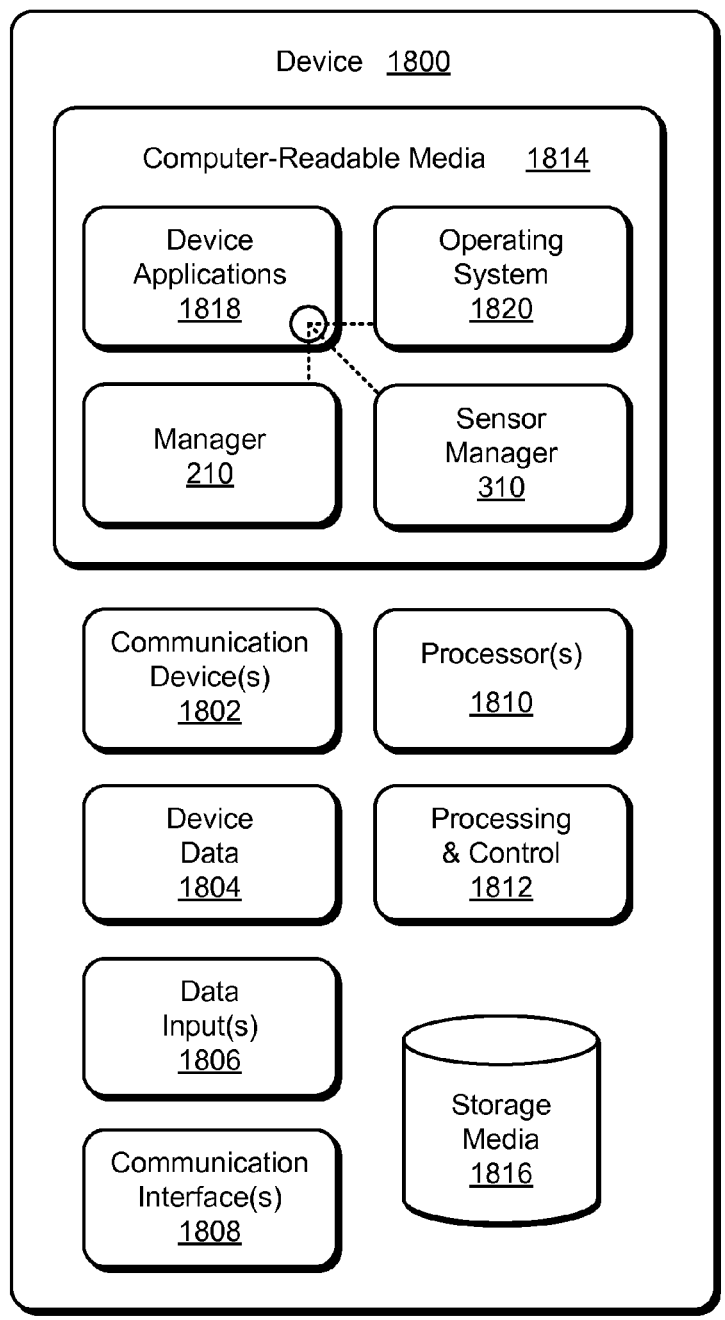
FIG. 18 illustrates an example device embodying, or in which techniques may be implemented that enable use of, noninvasive determination of cardiac pressure-volume loops of a human cardiovascular system and functional states of other physiological systems.

FIG. 18 illustrates various components of example computing system 1800 that can be implemented as any type of client, server, and/or computing device as described with reference to the previous FIGS. 1-17 to implement noninvasive determination of cardiac pressure-volume loops for a human cardiovascular system or functional states of other physiological systems. In embodiments, computing system 1800 can be implemented as one or a combination of a wired and/or wireless wearable device, System-on-Chip (SoC), and/or as another type of device or portion thereof. Computing system 1800 may also be associated with a user (e.g., a person) and/or an entity that operates the device such that a device describes logical devices that include users, software, firmware, and/or a combination of devices.

Computing system 1800 includes communication devices 1802 that enable wired and/or wireless communication of device data 1804 (e.g., received data, data that is being received, data scheduled for broadcast, data packets of the data, etc.). Device data 1804 or other device content can include configuration settings of the device, media content stored on the device, and/or information associated with a user of the device. Media content stored on computing system 1800 can include any type of audio, video, and/or image data, including complex or detailed results of human-health-monitoring acts. Computing system 1800 includes one or more data inputs 1806 via which any type of data, media content, and/or inputs can be received, such as human utterances, user-selectable inputs (explicit or implicit), messages, music, television media content, recorded video content, and any other type of audio, video, and/or image data received from any content and/or data source.

Computing system 1800 also includes communication interfaces 1808, which can be implemented as any one or more of a serial and/or parallel interface, a wireless interface, any type of network interface, a modem, and as any other type of communication interface. Communication interfaces 1808 provide a connection and/or communication links between computing system 1800 and a communication network by which other electronic, computing, and communication devices communicate data with computing system 1800.

Computing system 1800 includes one or more processors 1810 (e.g., any of microprocessors, controllers, and the like), which process various computer-executable instructions to control the operation of computing system 1800 and to enable techniques for, or in which can be embodied, noninvasive determination of cardiac pressure-volume loops for a human cardiovascular system or functional states of other physiological systems. Alternatively or in addition, computing system 1800 can be implemented with any one or combination of hardware, firmware, or fixed logic circuitry that is implemented in connection with processing and control circuits which are generally identified at 1812. Although not shown, computing system 1800 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Computing system 1800 also includes computer-readable media 1814, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Computing system 1800 can also include a mass storage media device 1816.

Computer-readable media 1814 provides data storage mechanisms to store device data 1804, as well as various device applications 1818 and any other types of information and/or data related to operational aspects of computing system 1800. For example, an operating system 1820 can be maintained as a computer application with computer-readable media 1814 and executed on processors 1810. Device applications 1818 may include a device manager, such as any form of a control application, software application, signal-processing and control module, code that is native to a particular device, a hardware abstraction layer for a particular device, and so on.

Device applications 1818 also include any system components, engines, or managers to implement the techniques. In this example, device applications 1818 include manager 210 or sensor manager 310.

CONCLUSION

Although embodiments of techniques using, and apparatuses enabling, noninvasive determination of cardiac pressure-volume loops for a human cardiovascular system or functional states and trends of other physiological systems have been described in language specific to features and/or methods, it is to be understood that the subject of the appended claims is not necessarily limited to the specific features or methods described. Rather, the specific features and methods are disclosed as example implementations of these techniques.

What is claimed is:

1. A method for health monitoring without interrupting a person's daily routine, the method comprising:
   executing a manager on a processor of a computing device to perform operations including: receiving, from multiple noninvasive health monitors configured to measure a physiological system of the person using a plurality of different modalities without interrupting the person's daily routine, sensor data for the person that corresponds the plurality of different modalities, the different modalities sensing different measurable conditions;
   determining a functional state of the physiological system of the person, the functional state comprising a cardiac pressure-volume loop for a cardiovascular system of the person, the functional state determined based on the sensor data received and by: correlating the sensor data of two or more particular modalities of the plurality of different modalities that are associated with the cardiac pressure-volume loop, the correlating including correlating the sensor data of a first of the two or more particular modalities with the sensor data of at least a second of the two or more particular modalities based on times the sensor data of the first and at least second particular modalities are recorded;

and combining the correlated sensor data of the first and at least second particular modalities to ascertain a measure indicative of the functional state; recording the functional state;

and determining, based on the functional state and previously recorded functional states for the physiological system of the person, a health trend for the physiological system of the person, the determined health trend being presentable via a user interface on a display of a computing device.

2. The method as described in claim 1, further comprising communicating at least one of the functional state or the health trend for the physiological system of the person to a medical professional associated with the person.

3. The method as described in claim 1, wherein the sensor data includes data from at least two of the multiple noninvasive health monitors and for a same time.

4. The method as described in claim 3, wherein the determining includes at least one of correlating or aggregating the sensor data of the first particular modality with the sensor data of the at least second particular modality that correspond to the same time.

5. The method as described in claim 1, wherein the plurality of different modalities includes two or more of reflected light, sound waves, electromagnetic sensing, radar, or fluid mechanics.

6. The method as described claim 1, wherein two or more of the multiple noninvasive health monitors actively sense the person's health.

7. The method as described in claim 6, wherein the person is not required to explicitly operate or actively interact with the two or more of the multiple noninvasive health monitors.

8. The method as described in claim 1, further comprising determining an additional functional state of a different physiological system of the person comprising a nervous, endocrine, muscular, skeletal, or integumentary system.

9. The method as described in claim 1, wherein the correlating correlates sensor data from one of the multiple noninvasive health monitors with sensor data from another of the multiple noninvasive health monitors based on sub-second precision relating to an element of the physiological system.

10. The method as described in claim 1, further comprising, responsive to the functional state exceeding a safety threshold, alerting the person or a medical professional associated with the person.

11. The method as described in claim 1, further comprising presenting the health trend for the person's physiological system on a mobile computing device associated with the person.

12. A method for health monitoring without interrupting a person's daily routine, the method comprising:

executing a manager on a processor of a computing device to perform operations comprising:

determining, based on first noninvasive sensor data sensed over a first time period, a first cardiac pressure-volume loop for a person, the first noninvasive sensor data being sensed using two or more particular modalities of a plurality of different modalities that sense different measurable conditions, the particular modalities being associated with pressure-volume loop determinations, and the determining includes combining the first noninvasive sensor data of a first of the particular modalities with the first noninvasive sensor data of at least a second of the particular modalities to ascertain the first cardiac pressure-volume loop for the person;

determining, based on second noninvasive sensor data sensed over a second time period, a second cardiac pressure-volume loop for the person, the second noninvasive sensor data being sensed using the particular modalities, and the determining includes combining the second noninvasive sensor data of the first particular modality with the second noninvasive sensor data of the at least second particular modality to ascertain the second cardiac pressure-volume loop for the person;

comparing the first and second cardiac pressure-volume loops to determine a change between the first and second cardiac pressure-volume loops for the person; and determining, based on the change between the first and second cardiac pressure-volume loops for the person, a health trend specified as a cardiovascular health improvement or decline, the health trend being presentable via a user interface on a display of a computing device.

13. The method of claim 12, wherein the first and second cardiac pressure-volume loops are not precise but the change accurately reflects the cardiovascular health improvement or decline.

14. The method of claim 12, wherein the first and second noninvasive sensor data are sensed through a mat on which the person stands.

15. The method of claim 12, wherein the first and second noninvasive sensor data are sensed through measurement of skin color variations indicating differential blood volume.

16. The method of claim 12, wherein the first and second noninvasive sensor data are sensed through a radar-field device.

17. A computing device comprising:

a display;

a transceiver operable to receive sensor data from a plurality of noninvasive health-monitoring devices;

one or more computer processors; and one or more non-transitory computer-readable storage media having instructions stored thereon that, responsive to execution by the one or more computer processors, implements a manager configured to:

receive, through the transceiver and from multiple noninvasive health-monitoring devices, sensor data for a physiological system of a person sensed via a plurality of different modalities that sense different measurable conditions, and having associated times at which each of the sensor data were sensed;

determine, based on the sensor data received and the associated times at which each of the sensor data were sensed, a functional state of the physiological system of the person, the functional state comprising a cardiac pressure-volume loop determined through:

correlation of the sensor data for two or more particular modalities of the plurality of different modalities that are associated with the cardiac pressure-volume loop, the correlation including correlating a first of the two or more particular modalities with at least a second of the two or more particular modalities based on the associated times; and combination of the correlated sensor data of the first and the at least second particular modalities to ascertain a measure indicative of the functional state;

determine, based on the functional state and previously recorded functional states for the physiological system of the person, a health trend for the physiological system; and present, through a user interface on the display of the computing device, the health trend for the physiological system.

18. The computing device of claim 17, wherein the functional state is a later-in-time pressure-volume loop for the person's heart, the previously recorded functional state is a prior-in-time pressure-volume loop for the person's heart, and the health trend indicates an increased or decreased inotropy or afterload, a more or less dilated or restrictive cardiomyopathy, an increased or decreased left ventricular hypertrophy, an improved or declined aortic or mitral stenosis, or an improved or declined aortic or mitral regurgitation.

* * * * *